US011761028B2

(12) United States Patent
Xiao et al.

(10) Patent No.: US 11,761,028 B2
(45) Date of Patent: Sep. 19, 2023

(54) METHODS OF SPECIFICALLY LABELING NUCLEIC ACIDS USING CRISPR/CAS

(71) Applicant: Drexel University, Philadelphia, PA (US)

(72) Inventors: Ming Xiao, Huntingdon Valley, PA (US); Jennifer McCaffrey, Collegeville, PA (US)

(73) Assignee: Drexel University, Philadelphia, PA (US)

( * ) Notice: Subject to any disclaimer, the term of this patent is extended or adjusted under 35 U.S.C. 154(b) by 935 days.

(21) Appl. No.: 16/341,735

(22) PCT Filed: Oct. 18, 2017

(86) PCT No.: PCT/US2017/057201
§ 371 (c)(1),
(2) Date: Apr. 12, 2019

(87) PCT Pub. No.: WO2018/075648
PCT Pub. Date: Apr. 26, 2018

(65) Prior Publication Data
US 2020/0048688 A1 Feb. 13, 2020

Related U.S. Application Data

(60) Provisional application No. 62/410,324, filed on Oct. 19, 2016.

(51) Int. Cl.
*C12Q 1/6827* (2018.01)
(52) U.S. Cl.
CPC ..... *C12Q 1/6827* (2013.01); *C12Q 2521/101* (2013.01); *C12Q 2521/307* (2013.01); *C12Q 2563/107* (2013.01)
(58) Field of Classification Search
CPC .................. C12Q 2521/307; C12Q 2563/107
See application file for complete search history.

(56) References Cited

U.S. PATENT DOCUMENTS

| | | | |
|---|---|---|---|
| 2014/0356867 A1 | 12/2014 | Peter et al. | |
| 2015/0344873 A1 | 12/2015 | Xiao et al. | |
| 2018/0320226 A1* | 11/2018 | Church | C12N 15/11 |

FOREIGN PATENT DOCUMENTS

| | | |
|---|---|---|
| WO | WO 2016/028843 A2 | 2/2016 |
| WO | WO 2016/061523 A1 | 4/2016 |
| WO | WO 2016/089920 A1 | 6/2016 |

OTHER PUBLICATIONS

McCaffrey, J. et al., CRISPR-CAS9 D10A nickase target-specific fluorescent labeling of double strand DNA for whole genome mapping and structural variation analysis, Nucl. Acids Res., vol. 44, e11, pp. 1-8 (Year: 2015).*
Michaeli, Y. et al., Toward Epigenetic Mapping of Human Chromosomes in Nanochannel Arrays, 18th International Conference on Miniaturized Systems for Chemistry and Life Sciences, proceedings, pp. 2538-2539 (Year: 2014).*
McCaffrey et al. "CRISPR-CAS9 D10A nickase target-specific fluorescent labeling of double strand DNA for whole genome mapping and structural variation analysis," Nucleic Acids Research, Oct. 19, 2015 (Oct. 19, 2015), vol. 44, No. 2: ell, pp. 1-8.
International Search Report and Written Opinion, dated Jan. 16, 2018 in corresponding international application No. PCT/US17/57201 filed Oct. 18, 2017.
Anton et al., Visualization of specific DNA sequences in living mouse embryonic stem cells with a programmable fluorescent CRISPR/Cas system, Nucleus, vol. 5(2): 163-72, Mar. 2014,.
Chan et al., A simple DNA stretching methods for fluorescence imaging of single DNA molecules, Nucleic Acids Research, vol. 34(17):e113, Sep. 2006.
Chen et al., Dynamic Imaging of Genomic Loci in Living Human Cells by an Optimized CRISPR/Cas System, Cell, vol. 155(7):1479-91, Dec. 2013.
Das et al., Single molecule linear analysis of DNA in nano-channel labeled with sequence specific fluorescent probes, Nucleic Acids Research, vol. 38(18):e177, Oct. 2010.
Deng et al., CASFISH: CRISPR/Cas9-mediated in situ labeling of genomic loci in fixed cells, PNAS, vol. 112(28):11870-5, Sep. 2015.
Jing et al., Automated high resolution optical mapping using arrayed, fluid-fixed DNA molecules, Proceedings of the National Academy of Sciences in the United States of America, vol. 95(14):8046-8051, Jul. 1998.
Jo et al., A single-molecule barcoding system using nanoslits for DNA analysis, Proceedings of the National Academy of Sciences in the United States of America, vol. 104(8):2673-2678, Feb. 2007.

(Continued)

*Primary Examiner* — Teresa E Strzelecka
(74) *Attorney, Agent, or Firm* — HOWSON & HOWSON, LLP; Colleen M. Schaller

(57) ABSTRACT

A method of detecting the length of an individual telomere is provided. In one embodiment, the method includes contacting genomic DNA with a guide RNA having a portion complementary to a telomere repeat sequence in the genomic DNA and with Cas9 nickase to produce a single-strand break in the genomic DNA at the telomere repeat sequence. The nicked DNA is contacted with a polymerase and fluorescently labeled nucleotide, wherein the fluorescently labeled nucleotide is incorporated into the nicked DNA at the telomere repeat sequence. The genomic DNA is contacted with a second nicking endonuclease which is specific for a sequence motif in the genomic DNA thereby producing a second nick in the genomic DNA at the motif sequence. The nicked DNA is contacted with a polymerase and second fluorescently labeled nucleotide of different color, wherein the second fluorescently labeled nucleotide is incorporated into the nicked DNA at the motif sequence location. The length of the telomere is detected by measuring the fluorescence of first fluorescently labeled nucleotide at the telomere repeat location, wherein the fluorescently labeled motif sequences are used as a barcode to identify the chromosome.

12 Claims, 17 Drawing Sheets

Specification includes a Sequence Listing.

(56) References Cited

OTHER PUBLICATIONS

Kaul et al., Five dysfunctional telomeres predict onset of senescence in human cells, Embo Reports, vol. 13(1):52-59, Jan. 2012.
Koike-Yusa et al., Genome-wide recessive genetic screening in mammalian cells with a lentiviral CRISPR-guide RNA library, Nature Biotechnology, vol. 32(3):267-273, Dec. 2013.
Kounovsky-Shafer et al., Presentation of large DNA molecules for analysis as nanoconfined dumbbells, Macromolecules, vol. 46(20):8356-8368, Oct. 2013.
Lam et al., Genome mapping on nanochannel arrays for structural variation analysis and sequence assembly, Nature Biotechnology, vol. 30(8):771-776, Aug. 2012.
Linardopoulou et al., Human subtelomeric WASH genes encode a new subclass of the WASP amily, PLoS Genetics, vol. 3(12):e237, Dec. 2007.
Mak et al., Defining a standard set of patient-centred outcomes for lung cancer, The European Respiratory Journal, vol. 48(3):852-860, Sep. 2016.
Marie et al., Integrated view of genome structure and sequence of a single DNA molecule in a nanofluidic device, Proceedings of the National Academy of Sciences in the United States of America, vol. 110(13): 4893-4898, Mar. 2013.
Noble et al., A fast and scalable kymograph alignment algorithm for nanochannel-based optical DNA mappings, Pios One, vol. 10(4):e01210905, Apr. 2015.
Qi et al., DNA sequence alignment by microhomology sampling during homologous recombination, Cell, vol. 160(5): 856-869, Feb. 2015.
Rigby et al., Labeling deoxyribonucleic acid to high specific activity in vitro by nick translation with DNA polymerase I, Journal of Molecular Biology, vol. 113(1):237-51, Jun. 1977.
Sriram et al., Direct optical mapping of transcription factor binding sites on field-stretched λ-DNA in nanofluidic devices, Nucleic Acids Research, vol. 42(10):e85, Jun. 2014.
Stong et al., Subtelomeric CTCF and cohesin binding site organization using improved subtelomere assemblies and a novel annotation pipeline, Genome Research, vol. 24(6): 1039-1050, Mar. 2014.
Tegenfeldt et al., From the Cover: The dynamics of genomic-length DNA molecules in 100-nm channels, Proceedings of the National Academy of Sciences in the United States of America, vol. 101(30):10979-10983, Jul. 2004.
Zou et al., Does a Sentinel or a Subset of Short Telomeres Determine Replicative Senescence?, Molecular Biology of the Cell, vol. 15(8):3709-3718, Aug. 2004.
Samassekou et al. (2010) Sizing the ends: normal length of human telomeres. Ann Anat, 192, 284-291.
Blackburn et al. (2015) Human telomere biology: A contributory and interactive factor in aging, disease risks, and protection. *Science*, 350, 1193-1198.
Aubert et al. (2012) Telomere length measurement-caveats and a critical assessment of the available technologies and tools. Mutat Res, 730, 59-67.
Vera et al. (2012) Beyond average: potential for measurement of short telomeres. *Aging*, 4, 379-392.
Montpetit et al. (2014) Telomere length: a review of methods for measurement. Nurs Res, 63, 289-299.
Samassekou et al. (2009) Individual Telomere Lengths in Chronic Myeloid Leukemia. Neoplasia, 11, 1146-IN1146.
Perner et al. (2003) Quantifying Telomere Lengths of Human Individual Chromosome Arms by Centromere-Calibrated Fluorescence in Situ Hybridization and Digital Imaging. The American Journal of Pathology, 163, 1751-1756.
Martens et al. (1998) Short telomeres on human chromosome 17p. Nature genetics, 18, 76-80.
Xiao et al. (2007) Rapid DNA mapping by fluorescent single molecule detection. Nucleic Acids Res., 35, 12.
Ambrosini et al. (2007) Human subtelomeric duplicon structure and organization. Genome Biol, 8, R151.
Ran et al. (2013) Genome engineering using the CRISPR-Cas9 system. NatProtoc, 8, 2281-2308.
Zhang et al. (2015) Off-target Effects in CRISPR/Cas9-mediated Genome Engineering, Mol Ther Nucleic Acids, 4, e264.
Xu et al. (2007) Human cancer cells harbor T-stumps, a distinct class of extremely short telomeres. Mol Cell, 28, 315-327.
Coppe et al. The senescence-associated secretory phenotype: the dark side of tumor suppression, Annu Rev Pathol 5, 99-118 (2010).
Davalos et al. Senescent cells as a source of inflammatory factors for tumor progression. Cancer Metastasis Rev 29, 273-283 (2010).
Jaskelioff et al. Telomerase reactivation reverses tissue degeneration in aged telomerase-deficient mice. Nature 469, 102-106 (2011).
Mak et al. Genome-Wide Structural Variation Detection by Genome Mapping on Nanochannel Arrays. Genetics 202, 351-362 (2016).
Riethman et al. Integration of telomere sequences with the draft human genome sequence. Nature 409, 948-951 (2001).
Riethman et al. Mapping and initial analysis of human subtelomeric sequence assemblies. Genome Research 14, 18-28 (2004).
Alkan et al. Limitations of next-generation genome sequence assembly. Nat. Methods 8, 61-65 (2011).
Youngman et al. The telomeric 60 kb of chromosome arm 4p is homologous to telomeric regions on 13p, 15p, 21p, and 22p. Genomics 14, 350-356 (1992).
Hastie et al. Rapid Genome Mapping in Nanochannel Arrays for Highly Complete and Accurate De Novo Sequence Assembly of the Complex *Aegilops tauschii* Genome. Plos One 8 (2013).
Baird et al. Extensive allelic variation and ultrashort telomeres in senescent human cells. Nat Genet 33, 203-207 (2003).
Britt-Compton et al. Structural stability and chromosome-specific telomere length is governed by cis-acting determinants in humans. Hum Mol Genet 15, 725-733 (2006).

* cited by examiner

Two color scheme

Nick-labeling motifs and CRISPR-Cas9 labeling of telomeres at the same time (Green labels)

Nick-labeling

5'...ATGCTCTTCNGTGATC...3' SEQ ID NO: 24
3'...TACGAGAAGNCACTAG...5' SEQ ID NO: 25

CRISPR-Cas9 labeling

SEQ ID NO: 26
5'...GGTTAGGGTTAGGGTTAGGGTTA
   GGGTTAGGGTTAGGG...3'

SEQ ID NO: 27
3'...CCAATCCCAATCCCAATCCCAAT
   CCCAATCCCAATCCC...5'

SEQ ID NO: 1 UUAGGGUUAGGGUU

Three color scheme

Nick-labeling motifs first (green)
CRISPR-Cas9 telomere labeling (red)

5'...ATGCTCTTCNGTGATC...3' SEQ ID NO: 24
3'...TACGAGAAGNCACTAG...5' SEQ ID NO: 25

SEQ ID NO: 26
5'...GGTTAGGGTTAGGGTTAGGGTTA
   GGGTTAGGGTTAGGG...3'

SEQ ID NO: 27
3'...CCAATCCCAATCCCAATCCCAAT
   CCCAATCCCAATCCC...5'

SEQ ID NO: 1 UUAGGGUUAGGGUU

Imaging in Nanochannels

Port
Pillars
Nanochannels

Telomere length calculation: align molecules to reference or de novo assembly to classify the molecules 5.39kb
13.87kb
8.63kb
4.11kb

FIG. 1

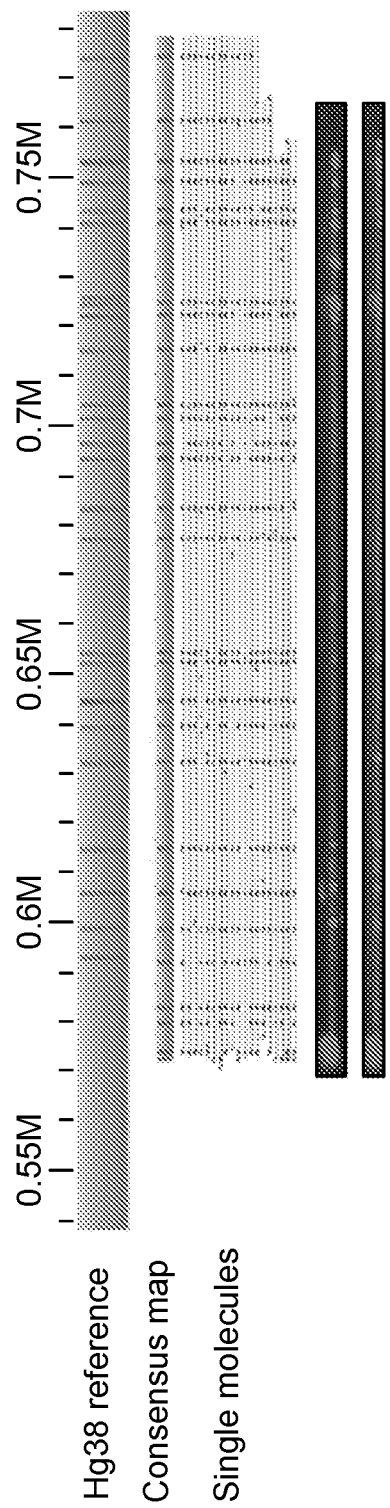

Indel haplotype

| | Deletion(−) | Insertion(+) | Deletion(−) | |
|---|---|---|---|---|
| | GCACGT......ACTGTTTCTTGTGTGGCTGAAACGGTGA.......CTGTGCTTGCAGTTG | | | Paternal |
| | GCACGTCGTACTGTTTACTGTTGTG.......AAACCGAGAGTCCTGTGCATGCAGTTG | | | Maternal |

| | Indel haplotype | SNP haplotype | Indel/SNP haplotype | |
|---|---|---|---|---|
| | − + − | TGT | −T+G−T | Paternal |

Indel/SNP haplotype

FIG. 7B

METHODS OF SPECIFICALLY LABELING NUCLEIC ACIDS USING CRISPR/CAS

CROSS-REFERENCE TO RELATED APPLICATIONS

This is a 371 of International Patent Application No. PCT/US2017/057201, filed Oct. 18, 2017, which claims the benefit under 35 USC 119(e) of U.S. Provisional Patent Application No. 62/410,324, filed Oct. 19, 2016. These applications are incorporated by reference herein.

STATEMENT REGARDING FEDERALLY SPONSORED RESEARCH OR DEVELOPMENT

This invention was made with government support under RO1 HG005946 and CA177395 awarded by National Institutes of Health. The government has certain rights in the invention.

INCORPORATION-BY-REFERENCE OF MATERIAL SUBMITTED IN ELECTRONIC FORM

Applicant hereby incorporates by reference the Sequence Listing material filed in electronic form herewith. This file is labeled ":DRX_16-1918USA_ST25.txt", created Mar. 13, 2023, and has a size of 6,696 bytes.

BACKGROUND OF THE INVENTION

In humans, telomeres are a nucleoprotein complex made up of tandem 5'-TTAGGG-3' repeats and associated proteins located at the ends of all 46 chromosomes. The G-rich strand ends with a 100-200 bp single stranded overhang that forms a telomere loop (t-loop) that is supported by a 6 protein complex called the shelterin. There are 92 telomeres in a diploid human cell ranging between 0.5 kb and kb. Telomeres prevent the ends of chromosomes from being recognized as broken which triggers DNA end-joining, recombination, or repair that can lead to chromosomal abnormalities and unstable chromosomes. Telomere lengths vary between cells, chromosomes within the same cell, and even homologous chromosome arms. Even though the lengths of telomeres are very heterogeneous, there have been documented trends. Telomeres on chromosome arms 17p, 19p, and 20q have been identified as some of the shortest, whereas 1p, 3p, 2p, and 4q contain among the longest. Telomere loss changes the telomere structure which eventually leads to replicative senescence or apoptosis.

Currently, there are several methods to measure the length of telomere repeats each with their own advantages and disadvantages. Terminal Restriction Fragment (TRF) estimates the average telomere length of a population of cells with a resolution of 1 kb. TRF requires a minimal amount of 1.5 micrograms of DNA, overestimates the telomere length by 2.5 to 4 kb, and is not sensitive to very short telomeres. The quantitative PCR (qPCR) method was developed to improve on the amount of DNA required with only 25-50 ng needed to measure telomere repeats, but still only provides mean telomere length information.

Single Telomere Length Analysis (STELA) and Quantitative Fluorescence in situ Hybridization (Q-FISH) were developed to detect and measure the length of specific telomeres. STELA generates highly accurate telomere measurements with DNA in the pictogram range or as few as 50 cells. STELA can measure critically short telomeres with a resolution of 0.1 kb and identify allelic differences in an individual telomere length. However, it is usually only performed on chromosomes XpYp, 2p, 11q, 12q, and 17p each in their own reaction. Quantitative fluorescence in situ hybridization (Q-FISH) of telomere repeats requires only 15-20 metaphase cells per sample and measures all individual chromosomes. This method is able to identify ends without detectable repeats (<0.5 kb) as well as chromosome fusion occurrences. The major disadvantage of Q-FISH is that it is limited in the analysis of cells currently in metaphase and is unable to measure telomeres in terminally senescent cells or cells that are no longer able to divide. In vitro and in vivo studies measuring mean telomere lengths have established a relationship between lower values of mean telomere length and an increase in age related diseases and mortality. There have been numerous studies that suggest the length of individual telomeres is an important factor in cell growth and many biological functions. It has been shown that the shortest telomere or a portion of the shortest telomeres rather than the average telomere length is critical for chromosome stability and cell viability. Therefore, it is important to measure the frequency of short telomeres to detect small changes in telomere length. Having a higher frequency of short telomeres has also been related to an increased risk of different cancers. The amount of critically short telomeres is likely to be a useful biomarker of aging and age related diseases. Gaining a better understanding of telomere lengths in healthy humans will lead to knowledge of their role in diseases. However, with the current methods to measure telomere length, it is impossible to measure all individual telomeres. Indeed, previous studies have been used to visualize telomere loci (Anton et al, Nucleus, 5(2):163-72 (March 2014); Deng et al, PNAS, 112(38): 11870-5 (September 2015)), including mean telomere length (Chen et al, Cell, 155(7):1479-91 (December 2013) using CRISPR systems. These methods are not able to measure individual telomeres and map them to the specific chromosomal locations.

SUMMARY OF THE INVENTION

Provided herein is method that simultaneously measures individual telomeres in a single reaction with the corresponding chromosome arms identified. In addition to measuring the telomere length, a method utilizing the same approach which is capable of identifying chromosomes with no detectable telomere repeats, chromosomal haplotypes, and previously unknown regions of the human genome is provided.

In one aspect, a method of detecting the length of an individual telomere is provided. In one embodiment, the method includes contacting genomic DNA with a guide RNA having a portion complementary to a telomere repeat sequence in the genomic DNA and with Cas9 nickase to produce a single-strand break in the genomic DNA at the telomere repeat sequence. The nicked DNA is contacted with a polymerase and fluorescently labeled nucleotide, wherein the fluorescently labeled nucleotide is incorporated into the nicked DNA at the telomere repeat sequence. The genomic DNA is contacted with a second nicking endonuclease which is specific for a sequence motif in the genomic DNA thereby producing a second nick in the genomic DNA at the motif sequence. The nicked DNA is contacted with a polymerase and second fluorescently labeled nucleotide of different color, wherein the second fluorescently labeled nucleotide is incorporated into the nicked DNA at the motif sequence location. The length of the telomere is detected by measuring the fluorescence of first fluorescently labeled nucleotide at the telomere repeat location, wherein the fluorescently labeled motif sequences are used as a barcode to identify the chromosome.

In another embodiment, the method includes contacting genomic DNA with a guide RNA having a portion complementary to the telomere repeat sequence in the genomic DNA and with Cas9 nickase to produce a single-strand break in the genomic DNA at the telomere repeat sequence. The genomic DNA is contacted with a second nicking endonuclease which is specific for a sequence motif in the genomic DNA thereby producing a second nick in the genomic DNA at the motif sequence. The nicked DNA is contacted with a polymerase and fluorescently labeled nucleotide, wherein the fluorescently labeled nucleotide is incorporated into the nicked DNA at the telomere repeat sequence and at the motif sequence. The length of the telomere is detected by measuring the fluorescence of first fluorescently labeled nucleotide at the telomere repeat location, wherein the second fluorescently labeled motif sequences are used as a barcode to identify the chromosome.

In another embodiment, the method includes contacting genomic DNA with a guide RNA having a portion complementary to the telomere repeat sequence in the genomic DNA and with Cas9 nickase to produce a single-strand break in the genomic DNA at the telomere repeat sequence. The nicked DNA is contacted with a polymerase and fluorescently labeled nucleotide, wherein the fluorescently labeled nucleotide is incorporated into the nicked DNA at the telomere repeat sequence. The genomic DNA is contacted with a second guide RNA having a portion complementary to a sequence in the subtelomeric region of the genomic DNA and with Cas9 nickase to produce a single-strand break in the genomic DNA at the subtelomeric sequence. The nicked DNA is contacted with a polymerase and second fluorescently labeled nucleotide, wherein the second fluorescently labeled nucleotide is incorporated into the nicked DNA at the subtelomeric sequence location. The length of the telomere is detected by measuring the fluorescence of first fluorescently labeled nucleotide at the telomere repeat location, wherein the fluorescently labeled subtelomeric sequence is used as a barcode to identify the chromosome.

In another embodiment, the method includes genomic DNA with a guide RNA having a portion complementary to the telomere repeat sequence in the genomic DNA and with Cas9 nickase to produce a single-strand break in the genomic DNA at the telomere repeat sequence. The genomic DNA is contacted with a second guide RNA having a portion complementary to a sequence in the subtelomeric region of the genomic DNA and with Cas9 nickase to produce a single-strand break in the genomic DNA at the subtelomeric sequence. The nicked DNA is contacted with a polymerase and fluorescently labeled nucleotide, wherein the fluorescently labeled nucleotide is incorporated into the nicked DNA at the telomere repeat sequence and at the subtelomeric sequence. The length of the telomere is detected by measuring the fluorescence of first fluorescently labeled nucleotide at the telomere repeat location, wherein the fluorescently labeled subtelomeric sequence is used as a barcode to identify the chromosome.

In one embodiment, the second guide RNA comprises multiple guide RNAs, each guide RNA having a portion complementary to a different target sequence in the subtelomeric region of the DNA, wherein each subtelomeric sequence is detected via fluorescent label, thus providing a barcode of a portion of the genomic DNA.

In another aspect, a method of detecting an individual haplotype is provided. The method includes contacting genomic DNA with a guide RNA having a portion complementary to a target genomic sequence directly adjacent to a protospacer adjacent motif (PAM), wherein the target genomic sequence or PAM sequence contain different alleles on the maternal or paternal genomic DNA. The method further includes contacting gRNA with Cas9 nickase to produce a single-strand nick in the genomic DNA at either maternal or paternal DNA containing the sequence perfectly complementary to the target genomic sequence or PAM sequence (matching alleles), wherein the either maternal or paternal DNA which does not have the perfectly complementary target genomic or PAM sequence is not nicked. The method further includes contacting the nicked DNA with a polymerase and fluorescently labeled nucleotide, wherein the fluorescently labeled nucleotides are incorporated into the nicked DNA at the target genomic or PAM sequence; and detecting the presence of the perfectly matching alleles by detecting the fluorescence of the first fluorescently labeled nucleotide at the target genomic or PAM sequence.

In one embodiment, the method includes the use of multiple gRNAs targeting multiple genomic loci directed sequences in which the maternal and paternal chromosomes have different alleles, matching alleles (perfectly complementary to the portion of gRNA, or PAM sequence), or mutant alleles (mismatches to the portion of gRNA, or a different allele in PAM sequences other than NGG).

In one embodiment, the method further includes contacting the genomic DNA with a second nicking endonuclease which is specific for a sequence motif in the genomic DNA thereby producing a second nick in the genomic DNA at the motif sequence. The nicked DNA is contacted with a polymerase and second fluorescently labeled nucleotide of different color, wherein the second fluorescently labeled nucleotide is incorporated into the nicked DNA at the motif sequence location. The fluorescently labeled motif sequences are used as a barcode to identify the chromosome.

In another aspect, a method of mapping genomic DNA is provided. The method includes contacting genomic DNA with a guide RNA having a portion complementary a first target sequence in the genomic DNA and with Cas9 nickase to produce a single-strand break in the genomic DNA at the first target sequence. The method further includes contacting the nicked DNA with a polymerase and fluorescently labeled nucleotide, wherein the fluorescently labeled nucleotide is incorporated into the nicked DNA at the first target sequence. The target sequence is a motif sequence found in the genomic DNA. In one embodiment, the genomic DNA is mapped to find areas of high density of the target sequence. In one embodiment, the target sequence is about 20 nucleotides in length, and the guide RNA has exact complementaritiy to the last 8, 9, 10, 11, 12, 13, or 14 bases of the 20nt target sequence.

Other aspects of the invention will be apparent from the description and examples below.

BRIEF DESCRIPTION OF THE DRAWINGS

FIG. 1 is a schematic graph illustrating both two color and three color telomere labeling schemes via the Cas9 D10A (Cas9n) directed by the telomere gRNA nicking the telomere repeats (TTAGG) and Nt.BspQI globally nicking the GCTCTTC motif. In the two color scheme all nicks were labeled with green fluorescently labeled nucleotides. In the three color scheme, the Nt.BspQI generated nicks were labeled with green fluorescently labeled nucleotides and the telomeres were labeled with red fluorescently labeled nucleotides. All samples were linearized in the nanochannels and optically imaged. De novo assembly was performed and the telomere label intensities were used for calculating the telomere length. The sequences displayed in the two color scheme and three color scheme are identical and are labeled in descending order as SEQ ID NOs: 24-27 and 1.

FIG. 5A is a graph of the single DNA molecules used to form the consensus map for chromosome 1p map to the 0.6 Mb region of the hg38 reference and all contain intense telomere end labels.

FIG. 7B is a graph showing an example of haplotype determination via Indel detected via CRISPR-Cas9 labeling. SNP haplotype could be combined to generate specific barcode patterns in order to differentiate the alleles. Paternal sequence is SEQ ID NO: 28. Maternal sequence is SEQ ID NO: 29.

DETAILED DESCRIPTION OF THE INVENTION

Figure 2A:
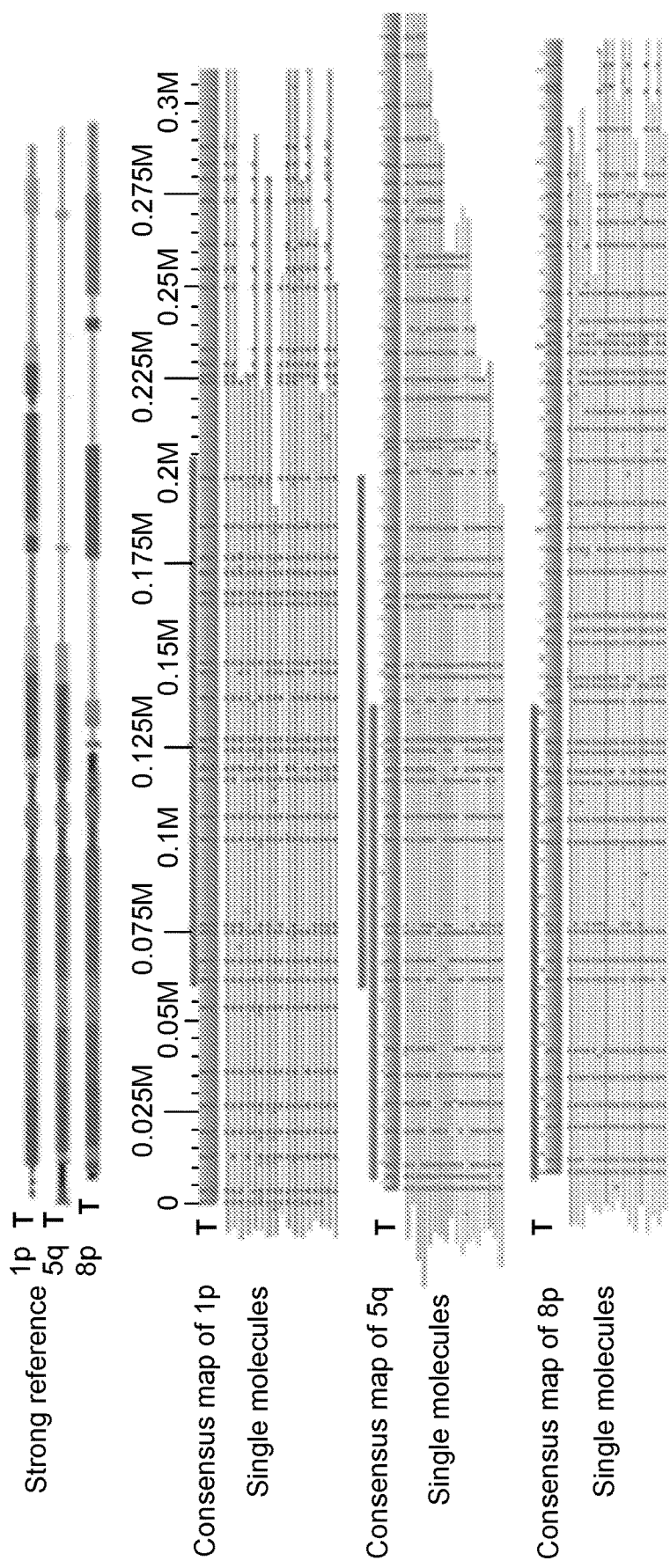
FIG. 2A is a graph of the labeling results of chromosomes 1p, 5q and 8p. The subtelomere repeat elements of 1p, 5q, and 8p are shown as shaded blocks from the Stong Reference. The telomeres are designated as a bold T. The consensus maps after de novo assembly and references are shown as light bars and the dark bars within these indicate the Nt.BspQI nick-label sites. The bars above the consensus maps designate the overlapping regions between the chromosome arms. The single molecules that comprise the respective consensus map are the lines shown directly below. The labels on the single molecules that align with the hg38 reference are dark and those that do not align are light.

The methods described herein used a modified CRISPR/Cas system. Clustered regularly interspaced short palindromic repeats (CRISPR) are segments of prokaryotic DNA containing short repetitions of base sequences. Each repetition is followed by short segments of "spacer DNA" from previous exposure to a bacteriophage virus or plasmid. CRISPR associated proteins (Cas) use the CRISPR spacers to recognize and cut these exogenous genetic elements in a manner analogous to RNA interference in eukaryotic organisms.

Recently, a new genome editing tool based on a bacterial CRISPR-associated protein-9 nuclease (Cas9) from *Streptococcus pyogenes* has been developed for generating double strand DNA breaks in vivo. To achieve site-specific DNA recognition and cleavage, the protein Cas9 must form a complex with a guide RNA (gRNA) comprised of a crRNA and a trans-activating crRNA (tracrRNA), which is partially complementary to the crRNA. The HNH and RuvC-like nuclease domains of Cas9 cut both DNA strands, generating double-stranded breaks (DSBs) at sites defined by a 20-nucleotide seed sequence within an associated crRNA transcript. Mutations of both nuclease domains generate nuclease-deficient Cas9 (dCas9) that is still capable of binding to gRNA and moving to the target sequence, and has been used to visualize repetitive DNA sequences. Other mutant forms which lack just the RuvC-like nuclease domain activity, only nick the DNA strand complementary to its crRNA, are characterized as Cas9 nickases (Cas9n). This type of mutant of Cas9 has been used with paired singled guide RNA (sgRNA) targeting opposite strands of the same locus to generate DSBs with great precision.

CRISPR/Cas9 can be used to modify any desired genomic target provided that sequence is unique compared to the rest of the genome and is located just upstream of a Protospacer Adjacent Motif (PAM sequence). A PAM sequence is a short stretch of DNA (typically 3-5 nucleotides) that serves as a binding signal for Cas9 and the presence of this sequence is a strict requirement for Cas9-mediated DNA cleavage.

Nicking

As used herein a "nickase" is an enzyme (e.g., an endonuclease) that causes breaks in one strand of the nucleic acid sequence ("nick"). Double-strand DNA breaks (DSB) occur or arise when both strands of the DNA duplex are severed. A "nick", also known as single-strand DNA break (SSB), can stimulate gene correction without the problems of DSB repair because the uncut DNA strand acts as a template to permit healing without alteration of genetic material.

A Cas9 nickase (also called Cas9n or, alternatively, Cas9) is used in the methods herein. In one embodiment, the Cas9 nickase is Cas9 D10A. Cas9 H840A is another nickase useful in the methods described herein. In one embodiment, the Cas9 nickase is a mutant protein, which contacts the dsDNA and makes a nick of a single strand. The Cas9 nickase generates a single-strand DNA break at a specific location based on a guide RNA-defined target sequence, rather than a double-strand DNA break ("cut") produced by the wild type enzyme. As used herein, the term "Cas9" is sometimes used interchangeably with "Cas9 nickase" or "Cas9 D10A". The use of Cas9 nickase for targeting and labeling DNA has been described. See, e.g., WO 2016/028843, which is incorporated herein by reference.

It is contemplated that other nucleases engineered to create nicks can be utilized in place of, or in conjunction with, the Cas9 described herein. Such endonucleases include, without limitation, homing endonucleases (HE), meganucleases, Transcription activator-like effector nuclease (TALEN), Zinc finger nuclease (ZFN), prokaryotic Argonaute (pAgo), and BurrH-based nuclease (BuDN). Homing endonucleases (HE) are double stranded DNases that have large, asymmetric recognition sites (12-40 base pairs) and coding sequences that are extremely rare and usually embedded in either introns or inteins. Single base changes do not abolish cleavage by HE but reduce its efficiency to variable extents. As a result, the observed sequence specificity of HE is typically in the range of 10-12 base pairs. Meganuclease are endodeoxyribonucleases characterized by a large recognition site (double-stranded DNA sequences of 12 to 40 base pairs), for example, I-SceI. Transcription activator-like effector nucleases (TALEN) are restriction enzymes that can be engineered to cut specific sequences of DNA. They are made by fusing a TAL effector DNA-binding domain to a DNA cleavage domain (a nuclease which cuts DNA strands). When combined with a nuclease, DNA can be cut at specific location. The restriction enzymes can be introduced into cells, for use in gene editing or for genome editing in situ.

Zinc-finger nucleases (ZFNs) are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. By taking advantage of endogenous DNA repair machinery, these reagents can be used to precisely alter the genomes of higher organisms and serve as a prominent tool in the field of genome editing.

Prokaryotic Argonaute (pAgo) is an endo-ribonuclease that uses a small RNA guide molecule to specifically target a complementary RNA transcript. Prokaryotic Argonautes are prokaryotic homologs of eukaryotic Argonaute proteins, which are key enzymes in RNA interference pathways. An Argonaute can bind and cleave a target nucleic acid by forming a complex with a designed nucleic acid-targeting nucleic acid. Cleavage can introduce double stranded breaks in the target nucleic acid. A nucleic acid can be repaired e.g. by endogenous non-homologous end joining (NHEJ) machinery. A piece of nucleic acid can be inserted. Engineering of non-genomic nucleic acid is also contemplated. Modifications of designed nucleic acid-targeting nucleic acids and Argonautes can introduce new functions to be used for genome engineering.

In some embodiments, the method includes contacting the genomic DNA with a motif-specific nicking endonuclease (also called "motif-specific nickase" or "motif-specific endonuclease") thereby producing a second nick in the genomic DNA at the motif sequence. As used herein a "motif" sequence refers to a short DNA sequence, which generally recurs in the genome. One of the major functions of motifs is indicating sequence-specific binding sites for proteins such as nucleases and transcription factors (TF).

The motif-specific nickase is used to nick the DNA at various locations where the motif is present. Such motif-specific endonucleases are known in the art and are characterized in that they only cut one strand ("nick") of the double stranded DNA, and are thus termed "nickases". In one embodiment, the motif-specific nickase is Nt.BspQI. In another embodiment, the nickase is selected from Nt.CviPII, Nt.AlwI, Nt.BsmAI, Nt.BstNBI, Nb.BsmI, Nb.BsrDI, Nb.BtsI, Nb.BbvCI and Nt.BbvCI. Other motif-specific nickases useful herein are contained in Table 1 below, with the motif sequence that they recognize. The appropriate nickase may be selected based on desired application and the portion of the DNA being surveyed.

TABLE 1

Nickases

| NICKASE | RECOGNITION SEQUENCE |
|---|---|
| Nt.AlwI | GGATC (4/none) |
| Nb.BbvCI | CCTCAGC (none/-2) |
| Nt.BbvCI | CCTCAGC (-5/none) |
| Nt.BhaIII | GAGTC (4/none) |
| Nb.Bpu10I | CCTNAGC (none/-2) |
| Nt.Bpu10I | CCTNAGC (-5/none) |
| Nt.Bpu10IB | CCTNAGC (-5/none) |
| Nb.BsaI | GGTCTC |
| Nt.BsaI | GGTCTC (1/none) |
| Nb.BsmI | GAATGC (none/-1) |
| Nb.BsmAI | GTCTC (none/5) |
| Nt.BsmAI | GTCTC (1/none) |
| Nt.BsmBI | CGTCTC (1/none) |
| Nt.BspD6I | GAGTC (4/none) |
| Nb.BspQI | GCTCTTC |
| Nt.BspQI | GCTCTTC (1/none) |
| Nb.BsrDI | GCAATG (none/0) |
| Nb.BssSI | CACGAG (none/-1) |
| Nt.Bst9I | GAGTC (4/none) |
| Nt.BstNBI | GAGTC (4/none) |
| Nt.BstSEI | GAGTC (4/none) |
| Nb.BtsI | GCAGTG (none/0) |
| Nb.BtsCI | GGATG |
| Nt.BtsCI | GGATG |
| Nt.CviPII | CCD (-3/none) |
| Nt.CviQII | RAG (-2/none) |
| Nt.CviQXI | RAG (-2/none) |
| V.Gel16401III | CGCG |
| Nt.MlyI | GAGTC (5/none) |
| Nb.Mva1269I | GAATGC (none/-1) |
| Nb.SapI | GCTCTTC |
| Nt.SapI | GCTCTTC |

In other embodiments, the method includes contacting the genomic DNA with a guide RNA having a portion complementary to a target sequence, which is a motif sequence.

In one embodiment of the method, the genomic DNA is contacted with a guide RNA having a portion complementary to a target sequence in the genomic DNA and with Cas9 nickase to produce a nick in the genomic DNA at a specific location adjacent to the target sequence. The nicked DNA is contacted with a polymerase and fluorescently labeled nucleotide, wherein the fluorescently labeled nucleotide is incorporated into the nicked DNA at the specific location. The method further includes contacting the genomic DNA with a motif-specific nicking endonuclease thereby producing a second nick in the genomic DNA at the motif sequence. The nicked DNA is contacted with a polymerase and second fluorescently labeled nucleotide of the same color or different color, wherein the second fluorescently labeled nucleotide is incorporated into the nicked DNA at the motif sequence location. In another embodiment, the DNA is contacted with the motif-specific nickase prior to contacting with the Cas9 nickase. In another embodiment, where the same fluorescently labeled nucleotide is used, the DNA is contacted with both nickases at about the same time.

As used herein, the term "guide RNA" may refer to the combination of a long, chemically synthesized trans-activating CRISPR RNA (tracrRNA) plus a chemically synthesized CRISPR RNA (crRNA), which is partially complementary to the gene target site of interest. The term "guide RNA" may also, in another embodiment, refer to an expressed single guide RNA (sgRNA) that consists of both the crRNA and tracrRNA as a single construct.

In one embodiment, a guide RNA has a portion which is complementary to the target sequence in the genomic DNA. The "seed sequence" is complementary to the target DNA sequence and is incorporated into the crRNA. The crRNA is used in conjunction with the universal tracrRNA. In one embodiment, the gRNA is created by pre-incubating the tracrRNA and crRNA prior to contacting with the Cas9 enzyme. In one embodiment, the crRNA and/or tracrRNA is chemically synthesized. In another embodiment, the crRNA and/or tracrRNA is in vitro transcribed. In yet another embodiment, the crRNA and/or tracrRNA is vector encoded and recombinantly produced.

In one embodiment, the gRNA (either sgRNA or crRNA/tracrRNA) is pre-incubated with the Cas9 before contacting with the genomic DNA to form a complex. In another embodiment, the gRNA and Cas9 are contacted with the DNA at approximately the same time.

In another embodiment, the guide RNA is expressed as a single guide RNA (sgRNA). In one embodiment, the sgRNA is chemically synthesized. In another embodiment, the sgRNA is in vitro transcribed. In yet another embodiment, the sgRNA is vector encoded and recombinantly produced.

Fluorescent Labeling

In the methods described herein, the DNA nicks are repaired using nucleotides which are fluorescently labelled, in conjunction with a DNA polymerase. The fluorescently labelled nucleotide is separately selected for both the Cas9 nick labeling step and the motif-specific nickase labeling step. That is, the same, or different fluorescent labelled nucleotides can be used for the Cas9 nick labeling step and the motif-specific nickase labeling step. Fluorescent labeling is a process of incorporating a fluorescent tag to a molecule or in a system to visualize the fluorescent tag, also known as a label or probe. Fluorescent dyes are covalently bound to biomolecules such as nucleic acids or proteins so that they can be visualized by fluorescence imaging. Suitable fluorescently labeled nucleotides are known in the art and include, without limitation, Alexa Fluor® 555-aha-dCTP, Alexa Fluor® 555-aha-dUTP, Alexa Fluor® 647-aha-dCTP, Alexa Fluor® 647-aha-dUTP, ChromaTide® Alexa Fluor® 488-5-dUTP, ChromaTide® Alexa Fluor® 546-14-dUTP, ChromaTide® Alexa Fluor® 568-5-dUTP, ChromaTide® Alexa Fluor® 594-5-dUTP, ChromaTide® Fluorescein-12-dUTP, ChromaTide® Texas Red®-12-dUTP, Fluorescein-aha-dUTP, DY-776-dNTP, DY-751-dNTP, ATTO 740-dNTP, ATTO 700-dNTP, ATTO 680-dNTP, ATTO 665-dNTP, ATTO 655-dNTP, OYSTER-656-dNTP, Cy5-dNTP, ATTO 647N-dNTP, ATTO 633-dNTP, ATTO Rho14-dNTP, ATTO 620-dNTP, DY-480XL-dNTP, ATTO 594-dNTP, ATTO Rho13-dNTP, ATTO 590-dNTP, ATTO Rho101-dNTP, Texas Red-dNTP, ATTO Thio12-dNTP, ATTO Rho12-dNTP, 6-ROX-dNTP, ATTO Rho11-dNTP, ATTO 565-dNTP, ATTO 550-dNTP, 5/6-TAMRA-dNTP, Cy3-dNTP, ATTO Rho6G-dNTP, DY-485XL-dNTP, ATTO 532-dNTP, 6-JOE-dNTP, ATTO 495-dNTP, BDP-FL-dNTP, ATTO 488-dNTP, 6-FAM-dNTP, 5-FAM-dNTP, ATTO 465-dNTP, ATTO 425-dNTP, ATTO 390-dNTP and MANT-dNTP. Suitable fluorescently labeled nucleotides also include dideoxynucleotides (ddNTPs). Each of the listed labels used with dNTPs is suitable for use with ddNTPs (e.g., ATTO 488-ddNTP) and is intended to refer to either a dNTP or ddNTP. Methods for nick-labeling are known in the art, and are described herein. See, e.g., Rigby, P. W. J., et al. [1977] J. Mol. Biol. 113:237, which is incorporated herein by reference.

In one embodiment, the fluorescent label used in the Cas9 labeling and the motif-specific labeling are different. In this embodiment, removal of the free nucleotides is performed. This can be accomplished by dialysis or via enzyme. Such methods are known in the art and are described in the examples. In one embodiment, the free nucleotides are removed via dialysis. In another embodiment, the free nucleotides are removed via enzyme. Such enzymes include shrimp alkaline phosphatase and pyrrolidonyl peptidase (PYRase).

It is intended that the fluorescently labeled nucleotides may be the same or different for each nicking reaction.

The nicked DNA is labeled using a DNA polymerase. In one embodiment, the DNA polymerase has exonuclease activity. Such DNA polymerases include, without limitation, Taq DNA Polymerase, E. coli DNA Polymerase I and Bst DNA Polymerase. In one embodiment, the polymerase is Taq DNA polymerase.

In one embodiment, the labeled DNA is repaired with a DNA ligase.

In another embodiment, the method includes RNAse treatment after the Cas9-dependent nicking step. In yet another embodiment, the method includes protease treatment.

In one embodiment, the DNA backbone is stained. Suitable dyes are known in the art and include, without limitation, YOYO-1, YOYO-3, YO-PRO-1, TOTO-1, TO-PRO-1, TO-PRO-3, TO-PRO-5, POPO, BOBO, JOJO, LOLO, ethidium bromide (EB), propidium iodide (PI), Hoechst 33342, 4', 6-diamidino-2-phenylindole (DAPI), acridine orange, 7-AAD, LDS 751, hydroxystilbamidine, PicoGreen, OliGreen, RiboGreen, SYTOX Green/Blue/Orange, SYTO, and SYBR.

Visualizing DNA

In one embodiment, the genomic DNA is linearized and visualized after labeling. Methods of single DNA molecule fluorescence imaging are known in the art and include use of, e.g., nanochannels, nanopores or nanogaps.

In one embodiment, after the DNA is labelled using the methods described herein, the DNA is visualized. In one embodiment, the DNA labeling is visualized using a nanochannel, nanopore or nanogap. Visualizing DNA or optical mapping typically relies on sequence-specific DNA modifications at short target sites followed by imaging via Total Internal Reflection Fluorescence (TIRF) Microscopy (Chan, T. F., et al. (2006). "A simple DNA stretching method for fluorescence imaging of single DNA molecules." Nucleic Acids Res 34(17): e113), super-resolution microscopy and other microscopies. These techniques can roughly be divided into three groups: stretching over a surface, stretching via confinement in nanochannels, or stretching via elongational flow in micro/nanochannels. See, e.g., Noble, C., et al. (2015). "A fast and scalable kymograph alignment algorithm for nanochannel-based optical DNA mappings." Plos One 10(4): e0121905); Chan, T. F., et al. (2006). "A simple DNA stretching method for fluorescence imaging of single DNA molecules." Nucleic Acids Res 34(17): e113; Jing, J., et al. (1998). "Automated high resolution optical mapping using arrayed, fluid-fixed DNA molecules." Proc Natl Acad Sci USA 95(14): 8046-8051, Das, S. K., et al. (2010). "Single molecule linear analysis of DNA in nanochannel labeled with sequence specific fluorescent probes." Nucleic Acids Res 38(18): e177; and Marie, R., et al. (2013). "Integrated view of genome structure and sequence of a single DNA molecule in a nanofluidic device." Proc Natl Acad Sci USA 110(13): 4893-4898, each of which is incorporated herein by reference in its entirety.

Variants of flow stretching are implemented by attaching a large bead at the end of the DNA (Sriram, K. K., et al. (2014). "Direct optical mapping of transcription factor binding sites on field-stretched lambda-DNA in nanofluidic devices." Nucleic Acids Res 42(10): e85) or by a DNA molecular tethering in both or a single end by chemical bonds (Qi, Z., et al. (2015). "DNA sequence alignment by microhomology sampling during homologous recombination." Cell 160(5): 856-869), each of which is incorporated herein by reference in its entirety.

Nanopore and nanogap are also utilized for stretching, linearizing and imaging single DNA molecular. When a nanopore is immersed in a conducting fluid and a potential (voltage) is applied across it, an electric current due to conduction of ions through the nanopore can be observed. The amount of current is very sensitive to the size and shape of the nanopore. The capacitance, conductance and permittivity profiles of the Sub-10 nm nanogap electrodes are able to differentiate complementary, non-complementary and single mismatch target hybridization.

Elongation due to confinement in nanochannels can be performed by confining the DNA in one dimension by using a nanoslit or in two dimensions by using a nanoscale channel. See, e.g., Tegenfeldt, J. O., et al. (2004). "From the Cover: The dynamics of genomic-length DNA molecules in 100-nm channels." Proc Natl Acad Sci USA 101(30): 10979-10983; and Lam, E. T., et al. (2012). "Genome mapping on nanochannel arrays for structural variation analysis and sequence assembly." Nat Biotechnol 30(8): 771-776; Jo, K., et al. (2007). "A single-molecule barcoding system using nanoslits for DNA analysis." Proc Natl Acad Sci USA 104(8): 2673-2678 and Kounovsky-Shafer, K. L., et al. (2013). "Presentation of large DNA molecules for analysis as nanoconfined dumbbells." Macromolecules 46(20): 8356-8368, each of which is incorporated herein by reference.

Methods of using nanochannel arrays are known in the art. See, e.g., Lam et al, cited above). Briefly, a nanofluidic chip is provided that contains nanochannels that keep long DNA molecules in a consistent, uniformly elongated state. Fluorescently labeled DNA molecules are drawn into the nanochannels, held still and imaged automatically on the multicolor Irys® instrument. After imaging, additional sets of DNA molecules are streamed into the nanochannels for imaging. This process is repeated many times until the DNA is depleted or the nanochannels are rendered unusable as a result of clogging.

The nanofluidic chip contains three sets of nanochannels, each consisting of ~4,000 channels that are 0.4 mm in length and 45 nm in diameter. Using 193-nm lithography in a nanofabrication process on the surface of a silicon substrate, nanochannel array chips are produced with precise diameters. DNA molecules in the 45-mm nanochannels cannot fold back on themselves and are forced by physical confinement to be in an elongated, linearized state.

As long DNA molecules in solution exist as coiled balls, a gradient region consisting of pillars and wider channels is placed in front of the nanochannels to allow the DNA molecules to uncoil as they flow toward the array. In this region, the physical confinement is sufficiently dense that the molecules are forced to interact with the pillars, yet sufficiently sparse that the DNA is free to uncoil. Once uncoiled, the DNA can then be efficiently flowed into the array in a linear manner, and visualized fluorescently.

As used herein, a "barcode" refers to a pattern of fluorescent labeling that is specific to a particular chromosome or portion of genomic DNA. For example, the specific pattern of fluorescence of the motif nick-labeling can identify the specific chromosome or portion of DNA being visualized. Alternatively, the pattern of nick labeling of both the motif-specific nick labeling and Cas9-dependent nick-labeling can be used to identity the specific chromosome or portion of DNA being visualized. Such barcodes are useful e.g., to determine the chromosome or DNA region being visualized.

Telomere Length

Telomere repeats are immediately distal to subtelomeric repeat elements (SREs) which are approximately 80% of the most distal 150 kb of human subtelomeres. Long SRE regions of about 150 kb have been identified in some alleles of various telomeres, whereas 7 telomeres have minimal or no SRE content. Read lengths of greater than 50 kb are required for assembling these regions using single-molecule sequencing, which is beyond the capability of current technology. Furthermore, the telomere repeat sequence (TTAGGG)n sequence lacks motif nicking sites recognized by currently available nicking endonucleases and therefore cannot be labeled with sequence-motif based methods.

In one embodiment, the CRISPR-Cas9 nick-labeling technology is combined with the nickase based nick-labeling procedure, described herein, to label telomeric repeats and subtelomeric regions separately. CRISPR-Cas9 labeling in conjunction with a global nickase enzyme motif-dependent labeling method allows for accurate telomere length measurement of each chromosome arm (FIG. 1).

In the examples below, a mutant form of Cas9, termed Cas9 D10A, which is catalytically modified, was used with a telomere targeting gRNA to nick-label the telomeric repeats. The labeled DNA molecules were linearized in nanochannels and optically imaged. The labels from the enzyme motif-dependent labeling step were mapped to a reference to identify the chromosomal location of the corresponding Cas9 D10A labeled telomere. The intensity of the telomeric labeling was used and converted into base pairs to calculate the telomere length. This method was developed as a two-color and three-color approach, as described herein. The method was also used to observe the shortening of telomeres in aging cell lines. In addition to measuring the telomere length, the method is useful for identifying chromosomes with no detectable telomere repeats, chromosomal haplotypes, and previously unknown regions of the human genome. The methods are similarly useful for genome mapping.

In one aspect, a method of detecting the length of an individual telomere is provided. In one embodiment of the method, the first 20 nucleotides of the gRNA are complementary to the 3' to 5' telomere repeat region which is followed immediately by the protospacer adjacent motif (PAM) NGG.

As noted above, several embodiments are provided which utilize different schemes to produce different "barcodes" for identification the specific chromosome being identified. In one embodiment, sometimes called the "3-color" method, the method includes contacting genomic DNA with a guide RNA having a portion complementary to the telomere repeat sequence in the genomic DNA and with a Cas9 nickase to produce a nick in the genomic DNA at the telomere repeat sequence. The nicked DNA is contacted with a polymerase and fluorescently labeled nucleotide, wherein the fluorescently labeled nucleotide is incorporated into the nicked DNA at the telomere repeat sequence.

The method further includes contacting the genomic DNA with a nicking endonuclease which is specific for a sequence motif ("a motif-specific nickase") in the genomic DNA thereby producing a second nick in the genomic DNA at the motif sequence. In one embodiment, the nick is made at the motif sequence in more than one location in the genome, e.g., throughout the genome. The nicked DNA is contacted with a polymerase and second fluorescently labeled nucleotide of different color, wherein the second fluorescently labeled nucleotide is incorporated into the nicked DNA at the motif sequence location. The length of the telomere is detected by measuring the fluorescence of first fluorescently labeled nucleotide at the telomere repeat location. The fluorescently labeled motif sequences are used as a barcode to identify the chromosome.

In this embodiment, where two different labeled nucleotides are used, after the first nick labelling step, the free nucleotides are removed, e.g., via dialysis or enzymatic treatment.

In one embodiment, the Cas9 nick labeling occurs first. In another embodiment, the motif-specific nick labeling occurs first.

In one embodiment, a guide RNA has a portion which is complementary to the telomere repeat sequence in the genomic DNA. There are 92 telomeres in a diploid human cell ranging between 0.5 kb and 20 kb, which are made up of the telomere repeat sequence (TTAGGG)n. In one embodiment, the seed sequence of 20 nucleotides complementary to the 3'-5' strand of the telomere (UUAGGGUUAGGGUUAGGGUU-SEQ ID NO: 1) is incorporated into the crRNA. Other appropriate seed sequences based on the telomere repeat sequence can be designed by the person of skill in the art.

In another embodiment, sometimes called the "two-color" method, the genomic DNA is contacted with a guide RNA having a portion complementary to the telomere repeat sequence in the genomic DNA, and with a Cas9 nickase to produce a single-strand break in the genomic DNA at the telomere repeat sequence. The genomic DNA is also contacted with a second nicking endonuclease which is specific for a sequence motif in the genomic DNA, thereby producing a second nick in the genomic DNA at the motif sequence. The nicked DNA is contacted with a polymerase and fluorescently labeled nucleotide, wherein the fluorescently labeled nucleotide is incorporated into the nicked DNA at the telomere repeat sequence and at the motif sequence.

The length of the telomere is detected by measuring the fluorescence of first fluorescently labeled nucleotide at the telomere repeat location and the fluorescently labeled motif sequences are used as a barcode to identify the chromosome. In this embodiment, the same fluorescent label is used to mark the motif sequences and the telomere sequences. In one embodiment, the telomere repeat sequence, the motif sequence, or both is present in more than one location in the genomic DNA.

In another embodiment, as an alternative, or in addition to, the motif-specific nickase, one or more additional guide RNAs are provided, which are complementary to one or more sequences in the genomic DNA other than the telomeric sequences. These gRNAs in combination with the Cas9 nickase can be used in a similar way to the motif-specific nickase to create a "barcode" to identify the chromosome. In one embodiment, the additional sequence is a sequence in the subtelomere region of the DNA. In another embodiment, multiple guide RNAs are provided to target multiple subtelomeric sequences. In one embodiment, the telomere repeat sequence, the subtelomeric sequence, or both is present in more than one location in the genomic DNA.

In one embodiment, the genomic DNA is contacted with a second guide RNA having a portion complementary to a sequence in the subtelomeric region of the genomic DNA and with Cas9 nickase to produce a single-strand break in the genomic DNA at the subtelomeric sequence. In one embodiment, the nicked DNA is contacted with a polymerase and second fluorescently labeled nucleotide, of a different color, wherein the second fluorescently labeled nucleotide is incorporated into the nicked DNA at the subtelomeric sequence location. The length of the telomere is detected by measuring the fluorescence of first fluorescently labeled nucleotide at the telomere repeat location, and the second fluorescently labeled subtelomeric sequence is used as a barcode to identify the chromosome.

In one embodiment, the second guide RNA comprises multiple guide RNAs, each guide RNA having a portion complementary to a different target sequence in the subtelomeric region of the DNA, wherein each subtelomeric sequence is detected via fluorescent label, thus providing a barcode of a portion of the genomic DNA.

In another embodiment, the DNA is nicked with both telomeric-directed Cas9 nickase and the subtelomeric-directed Cas9 nickase, and the same fluorescently labeled nucleotide is incorporated into the nicked DNA at the telomere repeat sequence and at the subtelomeric sequence. The length of the telomere is detected by measuring the fluorescence of the fluorescently labeled nucleotide at the telomere repeat location, and the fluorescently labeled subtelomeric sequence is used as a barcode to identify the chromosome.

For each of the methods described herein, it is intended that the Cas9 nick-labeling may be performed before or after the motif-endonuclease nick labeling. Where multiple gRNAs are used in conjunction with Cas9 (e.g., for telomeric and subtelomeric sequences), these steps may be performed together or separate, with either step coming first.

As discussed herein, two labeling schemes for measurement of telomere length were developed (FIG. 1). In both schemes, the same gRNA may be used to nick-label the telomeric repeats, and the subtelomeric regions are globally nick-labeled using an endonuclease which is specific for a sequence motif in the DNA. Such motif-specific endonucleases are known in the art and are characterized in that they only cut one strand ("nick") of the double stranded DNA, and are thus termed "nickases". In one embodiment, the motif-specific nickase is Nt.BspQI. In another embodiment, the nickase is selected from Nt.CviPII, Nt.AlwI, Nt.BsmAI, Nt.BstNBI, Nb.BsmI, Nb.BsrDI, Nb.BtsI, Nb.BbvCI and Nt.BbvCI. Other motif-specific nickases useful herein are contained in Table 1 above.

The nicked DNA is labeled using a DNA polymerase. In one embodiment, the DNA polymerase has exonuclease activity. Such DNA polymerases include, without limitation, Taq DNA Polymerase, *E. coli* DNA Polymerase I and Bst DNA Polymerase. In one embodiment, the polymerase is Taq DNA polymerase.

In one embodiment, when two differently labeled fluorescent nucleotides are used, the unused nucleotides from the first nick labeling step are removed prior to the second nick labeling step.

In one embodiment, sometimes referred to as the "two-color" scheme, the Cas9n and Nt.BspQI are incubated with the human genomic DNA and simultaneously nick their respective regions. In the examples below, all of these nicks were labeled with green fluorescently labeled nucleotides using Taq DNA polymerase.

In one embodiment, the labeled DNA is repaired with a DNA ligase.

In the three color scheme, as described in the examples below, the Nt.BspQI was first incubated with the human genomic DNA and nicks the CGTCTTC motif. These nicks were labeled with green fluorescently labeled nucleotides using Taq DNA polymerase. After removing unused green fluorescent nucleotides with Shrimp Alkaline Phosphatase (SAP), the labeled DNA molecules were nicked with Cas9n and labeled with red fluorescently labeled nucleotides again using Taq DNA polymerase. The labeled DNA molecules were linearized in the nanochannels and optically imaged. De novo assembly was performed using the unique Nt.BspQI patterns referenced to hg38 and individual DNA molecules assembled are used for calculating the telomere length. This allowed for the identification of the chromosome arms with the corresponding telomere.

In one embodiment, the length of the telomere is detected by imaging the labeled telomere, e.g., as discussed in the examples below. In one embodiment, the contour of telomeric labeling is used to calculate telomere length. In another embodiment, the intensity of telomeric labeling is used to calculate telomere length. When viewed in a DNA imaging system, the longer the telomere, the more pixels it occupies. However, the ends of DNA molecules tend to fold back on to themselves which affects the length measurements. More importantly, due to photon scattering, even with single point emitter, several pixels collected photons. Thus, use of the contour method is less desirable for a telomere length less than 1 kb. This was observed with the telomeric labeling of the 8*q* fosmid with 800 bp of telomeric repeats occupying the same amount of pixels as a single fluorophore. Thus, for smaller telomeres, the total intensity of the telomere labels is a desirable method of measurement.

In one embodiment, to calculate the length of the telomere, the intensity of fluorescence is compared to a standard. For example, DNA which incorporates telomeres of known length can be included visualized concurrent with the telomeres of unknown size, and the values compared. In another embodiment, the measurement is compared to a standard curve. Such values may be pre-existing based on prior data, or performed concurrent with the method. In another embodiment, background fluorescence is removed prior to calculation.

In another embodiment, other engineered nucleases, such as Homing endonucleases (HE), Meganuclease, Transcription activator-like effector nuclease (TALEN), Zinc finger nuclease (ZFN), prokaryotic Argonaute (pAgo), or BurrH-based nuclease (BuDN), described above, are used instead of, or in parallel with Cas9. The use of such nucleases is known in the art and can be substituted for the Cas9 or motif-dependent nuclease described herein.

The methods described herein can be modified to target any desirable genomic sequence. In such embodiments, the first set of gRNA together with Cas9 is designed to be complementary to, and target, any genomic sequence to generate a nick. The second set of gRNA-Cas9 complexes or nicking endonuclease can target any other desirable different genomic sequences than first set of gRNAs.

A decrease in the telomere length with later population doublings is detected because during each cell division telomeres become progressively shorter. It has been shown that a population of extremely short telomeres exist in human telomerase-positive human cancer cells and transformed fibroblast cells lacking tumor suppressor pathways. In fibroblasts with functional tumor suppressor pathways with or without telomerase these extremely short telomeres are rare.

Thus, in one aspect, a method of identifying a cancer cell is provided. The method includes detecting the length of the telomeres in the cell, or a portion thereof, using a method as described herein. The method further includes comparing the length of the telomeres to the length of telomeres to a standard. Such standards include a cancer cell, a healthy cell, an aging cell and a stem cell. In one embodiment, when one or more telomere is about 100 bp or more shorter as compared to a healthy cell, the cell is determined to be a cancer cell. In one embodiment, the method of identifying a cancer includes measuring the length of chromosome 8q.

The term "cancer" as used herein means any disease, condition, trait, genotype or phenotype characterized by unregulated cell growth or replication as is known in the art. A "cancer cell" is cell that divides and reproduces abnormally with uncontrolled growth. This cell can break away from the site of its origin (e.g., a tumor) and travel to other parts of the body and set up another site (e.g., another tumor), in a process referred to as metastasis. A "tumor" is an abnormal mass of tissue that results from excessive cell division that is uncontrolled and progressive, and is also referred to as a neoplasm. Tumors can be either benign (not cancerous) or malignant. The methods described herein are useful for the treatment of cancer and tumor cells, i.e., both malignant and benign tumors, so long as the cells to be treated have mitochondrial localization of the chaperones as described herein. In various embodiments of the methods and compositions described herein, the cancer can include, without limitation, breast cancer, lung cancer, prostate cancer, colorectal cancer, brain cancer, esophageal cancer, stomach cancer, bladder cancer, pancreatic cancer, cervical cancer, head and neck cancer, ovarian cancer, melanoma, acute and chronic lymphocytic and myelocytic leukemia, myeloma, Hodgkin's and non-Hodgkin's lymphoma, and multidrug resistant cancer. In one embodiment, the cancer is a drug resistant cancer.

In another embodiment, the first set of gRNA together with Cas9 can target any genomic sequence to generate a nick. Second set of gRNA-Cas9 complexes or nicking endonuclease can target any other different genomic sequences than first set of gRNAs. For example, Facioscapulohumeral muscular dystrophy (FSHD) is associated with the deletion of a chromosomal tandem repeat called D4Z4 near the end of chromosome 4 at the 4q35 location. The D4Z4 region is a polymorphic variable number tandem repeat (VNTR) array consisting of 3.3 kilobase units, and each unit encodes for the DUX4 gene. Unaffected individuals have a chromosome 4 D4Z4 array that has a span of 11 to 150 contiguous units. In individuals with FSHD, this D4Z4 repeat array is contracted to a range between one to 10 contiguous units. Thus, in one embodiment, the first gRNA will contact D4Z4 repeats and Nt.BspQI will contact the sequence motifs. The 3.3 kb D4Z4 repeats will be counted as labeled repeating units for diagnosis of FSHD. Thus, in another embodiment, a method of diagnosing FSHD in a subject, is provided. After nick-labeling and imaging the DNA as described above, the number of D4Z4 repeats are counted. A diagnosis of FSHD is provided when the number of D4Z4 repeats is about 10 or less.

In another embodiment, a method of diagnosing Fragile X Syndrome (FXS) in a subject is provided. FXS is caused by the expansion or lengthening of the FMR1 gene on the X chromosome. Thus, in one embodiment, one gRNA will contact FMR gene repeats and Nt.BspQI will contact the sequence motifs to localize the FMR gene in the whole genome. The lengthening of FMR1 gene can be determined by the labeling intensity, as described herein. After nick-labeling and imaging the DNA as described above, the length of the FMR1 gene is determined. A diagnosis of FXS is provided when the length of the FMR1 gene is greater than the length of the FMR1 gene of a control.

Haplotypes

In another aspect, a method of determining individual haplotypes is provided. Each person has two copies of all chromosomes, except the sex chromosomes in males. A single-nucleotide polymorphism, often abbreviated to SNP, is a variation in a single nucleotide that occurs at a specific position in the genome, where each variation is present to some appreciable degree within a population (e.g. >1%). For each SNP, the combination of alleles a person has is called a genotype. The alleles of nearby SNPs on a single chromosome are correlated. A sequence of consecutive alleles on a particular chromosome is known as a haplotype. Currently, there is no good way to obtain haplotype over long distance (>10Kb).

Haplotype information has a crucial role in diverse contexts, including linkage analysis, association studies, population genetics and clinical genetics. A long distance target haplotyping method was developed based on CRISPR-Cas9 genome editing system, as described herein.

In the CRISPR/Cas system, guide RNAs target a 20 bp target sequence, and transport Cas9 to for gene editing. However, no editing can occur at any site other than one at which there is a protospacer adjacent motif (PAM) NGG immediately following the 20 bp recognition sequence. On embodiment of the haplotyping method is based upon this requirement. When of one of G base in the PAM motif (NGG) has an alternative allele on the other haplotype chromosome, then the Cas9 will not bind that haplotype chromosome for genome editing. However, the Cas9 is still able to bind and nick the haplotype containing the G allele. As used herein, this type of SNP is called a "PAM SNP", where G is the wild type allele and the other allele is the mutant allele.

In another embodiment, where a heterozygous indel is found within the 20 bp gRNA recognition sequence between maternal and paternal chromosome; the CRISPR-Cas9 will preferentially target the DNA strand with perfect complementary sequences for genome editing. As used herein, this type of indel is called a "gRNA-target indel", which has two different alleles, mutant allele and wild type allele.

In yet another embodiment, where any heterozygous mutation is found within the 20 bp gRNA recognition sequence between maternal and paternal chromosome; the CRISPR-Cas9 will preferentially target the DNA strand with perfect complementary sequences for genome editing. As used herein, this type of mutation is called a "gRNA-target mutation", which has two different alleles, mutant allele and wild type allele.

As used herein, the terms "complementary", "complementarity" and "complement" have the same meaning as commonly used. Complementarity is a property shared between two nucleic acid sequences, such that when they are aligned antiparallel to each other, the nucleotide bases at each position will be complementary.

In one embodiment, the method of detecting an individual haplotype includes contacting genomic DNA with a guide RNA having a portion complementary to a target genomic sequence which is directly adjacent to a protospacer adjacent motif (PAM), wherein PAM sequence contains wild type and mutant alleles on the maternal or paternal genomic DNA. The gRNA is contacted with Cas9 nickase to produce a single-strand nick in the genomic DNA at either the maternal or paternal DNA which contains the while type PAM allele. The other chromosome, which has a mutant PAM allele is not nicked by the Cas9 nickase.

The nicked DNA is contacted with a polymerase and fluorescently labeled nucleotide, and the fluorescently labeled nucleotides are incorporated into the nicked DNA at the target genomic or PAM sequence. The presence of the wild type PAM allele is detected by detecting the fluorescence of the fluorescently labeled nucleotide at the PAM sequence. The presence of the PAM mutant allele is not labeled. The wild type allele and mutant allele are distinguished.

In one embodiment, the method of detecting an individual haplotype includes contacting genomic DNA with a guide RNA having a portion complementary to a target genomic sequence which is directly adjacent to a protospacer adjacent motif (PAM), wherein the target sequence contains wild type and mutant alleles on the maternal or paternal genomic DNA. The gRNA is contacted with Cas9 nickase to produce a single-strand nick in the genomic DNA at either the maternal or paternal DNA which contains the gRNA-target wild type allele. The other chromosome, which has a gRNA-target mutant allele, is not nicked by the Cas9 nickase.

The nicked DNA is contacted with a polymerase and fluorescently labeled nucleotide, and the fluorescently labeled nucleotides are incorporated into the nicked DNA at the target genomic sequence. The presence of the gRNA-target wild type allele is detected by detecting the fluorescence of the fluorescently labeled nucleotide at the target genomic sequence. The presence of gRNA-target mutant allele is not labeled. The wild type allele and mutant allele are distinguished.

In another embodiment, the gRNA can be designed to match perfectly to the gRNA-target mutant alleles. In one embodiment, the method of detecting an individual haplotype includes contacting genomic DNA with a guide RNA having a portion complementary to a target genomic sequence which is directly adjacent to a protospacer adjacent motif (PAM), wherein target sequence contains wild type and mutant alleles on the maternal or paternal genomic DNA. The gRNA is contacted with Cas9 nickase to produce a single-strand nick in the genomic DNA at either the maternal or paternal DNA which contains the gRNA-target mutant allele. The other chromosome, which has a gRNA-target wild type allele is not nicked by the Cas9 nickase.

The nicked DNA is contacted with a polymerase and fluorescently labeled nucleotide, and the fluorescently labeled nucleotides are incorporated into the nicked DNA at the target genomic sequence. The presence of gRNA-target mutant allele is detected by detecting the fluorescence of the fluorescently labeled nucleotide at the target genomic sequence. The presence of the gRNA-target wild type allele is not labeled. The wild type allele and mutant allele are distinguished.

When designing the guide RNA to detect a PAM SNP, the target sequence will be the ~20 bp directly 5' to the position of the PAM allele. When designing the guide RNA to detect a gRNA-target mutation, the gRNA-target mutation will be found within the target sequence ~20 bp directly 5' to the position of the PAM motif When designing the guide RNA to detect a gRNA-target indel, the indel allele will be found within the target sequence ~20 bp directly 5' to the position of the PAM motif.

In one embodiment, the genomic DNA is contacted with multiple gRNAs targeting multiple genomic loci directed to more than one SNP (PAM SNP, gRNA-target indel or gRNA-target mutation). The combination of different alleles detected on multiple loci will allow the separation of maternal and paternal chromosome it individual haplotypes.

In another embodiment, the gRNA targets alleles which are the same in both the maternal and paternal DNA.

In another embodiment, the genomic DNA is further contacted with a second nicking endonuclease which is specific for a sequence motif in the genomic DNA thereby producing a second nick in the genomic DNA at the motif sequence. The nicked DNA is contacted with a polymerase and second fluorescently labeled nucleotide of the same color or different color, and the second fluorescently labeled nucleotide is incorporated into the nicked DNA at the motif sequence location, wherein the fluorescently labeled motif sequences are used as a barcode to identify the chromosome.

In one embodiment, the guide RNA comprises a crRNA and a tracrRNA, as discussed above. In another embodiment, the guide RNA is a single gRNA sequence, as discussed herein.

Genome Mapping

In one embodiment, the system described herein is used to map the whole genome, or a portion thereof. Such application is useful for analyzing gene regulation on a genome-wide scale. In one embodiment, the method is useful to determine whole genome patterns associated with one specific sequence motif, or several sequence motifs. In another embodiment, the whole genome is mapped to find areas of high density associated with one or more sequence motifs. The sequence motifs are generally based on repetitive sequences.

In one embodiment, a method of mapping genomic DNA is provided. The method includes contacting genomic DNA with a guide RNA having a portion complementary a first target sequence in the genomic DNA and with Cas9 nickase to produce a single-strand break in the genomic DNA at the first target sequence. The nicked DNA is contacted with a polymerase and fluorescently labeled nucleotide, and the fluorescently labeled nucleotide is incorporated into the nicked DNA at the first target sequence. In one embodiment, the target sequence comprises a motif sequence found in the genomic DNA.

As discussed above, no editing can occur at any site other than one at which there is a protospacer adjacent motif (PAM) NGG immediately following the 20 bp recognition sequence. Thus, in this embodiment, the motif sequence is one that is immediately followed by a PAM sequence. The mapping scheme is initialized via design of a 20 base pair (bp) sequence, which is immediately flanked by a PAM sequence, represented by the trinucleotide, NGG. In this aspect, the focus is on the seed sequence, which is the 10-12 bp immediately adjacent to the PAM motif, in which perfect, or near perfect, complementarity is critical. Evidence for the dramatic decrease in targeting frequency has been observed in a gRNA specific for the human Alu element, a transposable element which has over 1 million copies dispersed throughout the human genome. With a novel algorithm, changing any one of the seed bases drops the frequency of targeting from 300,000 sites to just 4,000. In other words, the target for the probe is 23 bp total, with the first 20 bp designed by the user and targeted by the guide RNA (with the 12 bp seed sequence being a part of the 20) with the remaining NGG within the template genome itself. Thus, in one embodiment, the target sequence is about 20 nucleotides in length. In another embodiment, the target sequence includes the PAM sequence.

To maximize the number of motif sequences which may be targeted using a single guide RNA, the guide RNA is designed to allow for 1-2 base pair mismatches in the first 8 bases of the sequence, as compared to the targeted sequence. However, the guide RNA sequence has exact complementarity to the last 7, 8, 9, 10, 11, 12, 13 or 14 bases of the 20nt target sequence. In one embodiment, the guide RNA sequence has exact complementarity to the last 7 bases of the 20nt target sequence. In one embodiment, the guide RNA sequence has exact complementarity to the last 8 bases of the 20nt target sequence. In one embodiment, the guide RNA sequence has exact complementarity to the last 9 bases of the 20nt target sequence. In one embodiment, the guide RNA sequence has exact complementarity to the last 10 bases of the 20nt target sequence. In one embodiment, the guide RNA sequence has exact complementarity to the last 11 bases of the 20nt target sequence. In one embodiment, the guide RNA sequence has exact complementarity to the last 12 bases of the 20nt target sequence. In one embodiment, the guide RNA sequence has exact complementarity to the last 13 bases of the 20nt target sequence. In one embodiment, the guide RNA sequence has exact complementarity to the last 14 bases of the 20nt target sequence. In preliminary whole-genome mapping work, it was found that less than 10% of the designed probe target sequences have a single base mismatch in the human genome, which can be discriminated with CRISPR-Cas9 labeling. Thus, a less than 1% false positive rate was achieved, while maintaining over 90% labeling efficiency.

In another embodiment, multiple guide RNAs are used to target additional motif sequences. In one embodiment, different motif sequences are targeted using different guide RNAs to ensure the all, or mostly all, of the variations of a motif are labeled. This way, one can achieve certain labeling density across whole genome.

In one embodiment, two guide RNAs are used. In another embodiment, three guide RNAs are used. In another embodiment, four guide RNAs are used. In another embodiment, five guide RNAs are used. In another embodiment, 6 guide RNAs are used. In another embodiment, 7, 8, 9 or 10 guide RNAs are used.

In one embodiment, when multiple guide RNAs are used to target the "same" motif, either a single fluorescently labeled nucleotide can be used or multiple fluorescently labeled nucleotides to determine where the variations are. For example, the nicking reaction can be accomplished using all of the guide RNAs together or in sequence prior to incorporating a fluorescently labeled nucleotide. In another embodiment, each guide RNA is used sequentially, with the fluorescently labeled nucleotide being incorporated prior to the nicking with the next guide RNA.

In another embodiment, the genome mapping method may be used with multiple guide RNAs that target different motif sequences. In such case it may be desirable to use differently labeled florescent nucleotides. The following examples illustrate several aspects and embodiments of the invention.

EXAMPLE 1

Preparation of DNA Samples and Guide RNA

Target sequence-specific labeling with Cas9n fluorescent nick-labeling was carried out on the BAC clone CH17-353B19, fosmids carrying cloned telomere-terminal DNA fragments ending in several hundred bases of $(TTAGGG)_n$ (Stong, N., et al. (2014). "Subtelomeric CTCF and cohesin binding site organization using improved subtelomere assemblies and a novel annotation pipeline." Genome Res 24(6): 1039-1050), an HIV-1 entire genome-containing plasmid pEcoHIV-NL4-3-eLuc (gift from Dr Won-Bin Young at University of Pittsburgh) and genomic DNA isolated from human B-Lymphocyte cells NA12878 (Corriel Research Institute, N.J., USA).

The seed sequence of 20 nucleotides complementary to the 3'-5' strand of the target template DNA were designed via a gRNA design tool (Feng Lab CRISPR Design Web Tool at crispr.mit.edu). Each seed sequence was incorporated into the crRNA. Two crRNAs for the genomic sequences of DUF1220 domain (in BAC clone), 1 for the telomere repeat sequence $(TTAGGG)_n$ and 7 for subtelomeric sequences, along with the universal tracrRNA, were synthesized by GE Dharmacon. The fosmid and CH17-353B19 gRNAs were created by pre-incubating the tracr-RNA(0.5 nmol) and corresponding crRNA(0.5 nmol) with 1× NEB Buffer 3 and 1× BSA at 4° C. for 30 min.

Three single guide RNAs (sgRNAs) containing seed sequence targeting HIV-1 structural gene regions (Gag, Pol and Env) were designed for efficiency and specificity using bioinformatics analysis tools. All the oligonucleotides for each target sequence (Table 3, Also see, Sequence Listing, which is incorporated by reference herein.) were synthesized in Alpha DNA (Montreal, Canada) and cloned into pKLVWG-sgRNA vector modified from pKLV-U6gRNA (BbsI)-PGKpuro2ABFP vector, a gift from Kosuke Yusa (Addgene plasmid #50946) (Koike-Yusa, H., et al. (2014). "Genome-wide recessive genetic screening in mammalian cells with a lentiviral CRISPR-guide RNA library." Nat Biotechnol 32(3): 267-273). The vector was digested with BbsI and treated with Antarctic Phosphatase, and the linearized vector was purified with the QIAquick® nucleotide removal kit (QIAGEN®). A pair of oligonucleotides for each targeting site was annealed, phosphorylated and ligated to the linearized vector. The sgRNA expression cassette was validated by sequencing with U6 sequencing primer in GENEWIZ®. The validated vector was used as template for PCR with forward T7-U6 and reverse sgRNA primer to generate T7 promoter-driven gRNA expression cassette. Then the sgRNA for each target was in vitro transcribed using MEGAshortscript™ T7 transcription kit (Life Technology®). The quality of HIV-1 sgRNAs was verified by electrophoresis in 5% denaturing polyacrylamide gel.

TABLE 3

Sequences for gRNAs.

| Loci | Loci number | Sequence 5'-3' | Type | SEQ ID NO. |
|---|---|---|---|---|
| DUF1220 | 1-12 | AAGUUCCUUUUAUGCAUUGG | gRNA | 2 |
| HIV plasmid | 1 | CACCGCAGGATATGTAACTGACAG | sgRNA | 3 |
|  | 2 | CACCGGCCAGATGAGAGAACCAAG | sgRNA | 4 |
|  | 3 | CACCGAGAGTAAGTCTCTCAAGCGGs | gRNA | 5 |
| Chr1q telomere | 1 | UUAGGGUUAGGGUUAGGGUU | gRNA | 6 |
| Chr1q subtelomere | 1 | CCCCUGUUGCCAGAGCCAGU | gRNA | 7 |
|  | 2 | GUAUUUAGUCAGAGGGCUAG | gRNA | 8 |
|  | 3 | AUACAGUAGGAUAACCGCAA | gRNA | 9 |
| Chr15q subtelomere | 1 | ACCUUGCUACCACGAGAGCA | gRNA | 10 |
|  | 2 | UCCAUUGGUUUAAUUAGGAA | gRNA | 11 |
| Chr11q subtelomere | 1 | GGUCCACCCUACGAUGUGC | gRNA | 12 |
|  | 2 | AGAUCAGCAGCCACGUGUGC | gRNA | 13 |
| Chr12p subtelomere | 1 | ACCUUGCUACCACGAGAGCA | gRNA | 14 |
|  | 2 | UCCAUUGGUUUAAUUAGGAA | gRNA | 15 |
| Alu | 1 | UGUAAUCCCAGCACUUUGGG | gRNA | 16 |

Loci numbers designate the labels from left to right in FIGS. 3-5.

EXAMPLE 2

Cas9n Fluorescent Nick-Labeling of Fosmids, HIV-1 Plasmid and BAC Clone CH17-353B19

The gRNAs or sgRNAs (5 μM) were incubated with 600 ng of Cas9n D10A (PNA Bio Inc), 1× NEB Buffer 3 and 1× BSA (NEB) at 37° C. for 15 min. The DNA (500 ng) was added to the mixture and incubated at 37° C. for 60 min. The nicked DNA was then labeled with 4.12 units of DNA Taq Polymerase (NEB), 0.1 μM of ATTO-532 dUTP dAGC and 1× Thermopol Buffer (NEB) at 72° C. 60 min. The labeled fosmids and BACs were cut and linearized with 5 units of NotI enzyme (NEB) at 37° C. for 60 min. The labeled pecoHIV-NL4-3-eLuc plasmid (17,099 bp) was digested with 20 units of a unique restriction enzyme EcoRI (at 5744 bp) (NEB). NotI and EcoRI were inactivated at 65° C. for 20 min.

The distances were calculated between spots using ImageJ. The histogram of the label distributions were plotted in Excel. If the pattern matched the predicted pattern we considered the labels as true positives. Missing labels were used for the calculation of labeling efficiency and the extra labels were used for calculating the false positive percentage.

Figure 3A:
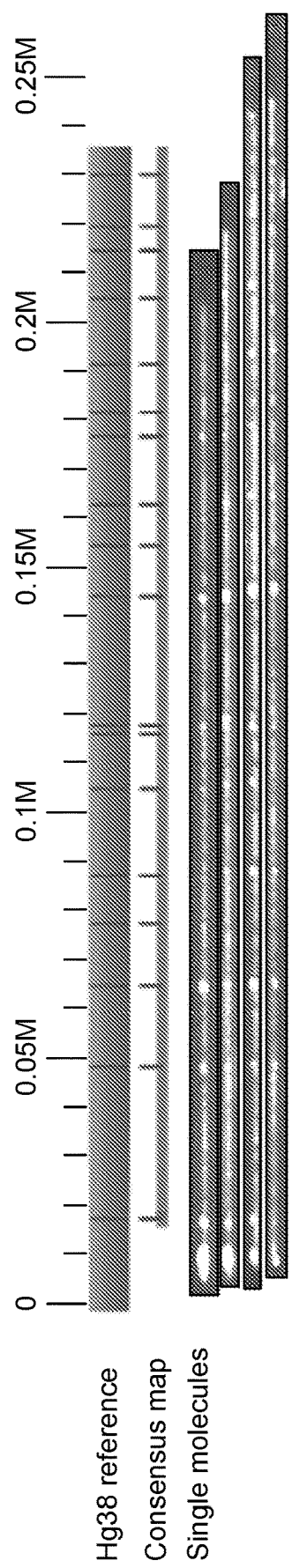
FIG. 3A is graph showing three color labeling results for chromosomes 3p of sample GM11832. The individual molecules were de novo assembled into the consensus maps which were mapped back to the hg38 reference. The bars on the consensus maps are Nt.BsPQI (CGTCTTC) sites that align to the corresponding reference site. A few of the single molecules that make up the consensus maps are shown (DNA backbone, labeled Nt.BsPQI sites (bright points all along backbone), and telomere (bright spots on left side)).

To establish the Cas9n fluorescent nick-labeling conditions and investigated the labeling efficiency with BAC clones, fosmids and plasmids as model systems. The Cas9n fluorescent nick-labeling of HLS DUF1220 triplets on a BAC clone were assessed (FIG. 3A). A single copy of HLS DUF1220 triplet spanned about 4.7 kb, and there were 12 copies on the BAC clone CH17-353B19. A gRNA probe was designed to target one unit of the triplets. Clearly, there were 12 copies detected on this 240 kb BAC clone and the distance between the each triplet measured 4.7 kb, which was in a good agreement with the clone sequence. The labeling efficiency of each locus was determined by evaluating 192 labeled BAC molecules, ranging from 87% to 98%. Interestingly, the middle copies (#6-8 labels from the left most one in FIG. 3A) were labeled at lower labeling efficiency.

The Cas9n fluorescent nick-labeling was very specific. The extra labels outside of the DUF domain were used to calculate the false positives in FIG. 3A. The spurious labels inside the DUF domain were harder to define because the DNA molecules inside the nanochannel were not static. Their slight movements and the limitation of optical resolution may cause inaccurate measurement of 4.7 kb repetitive sequences during the imaging time (200 ms). When all of the spurious spots inside and outside of the DUF domain were used, the false positive percentage is 0.6%.

Figure 3B:
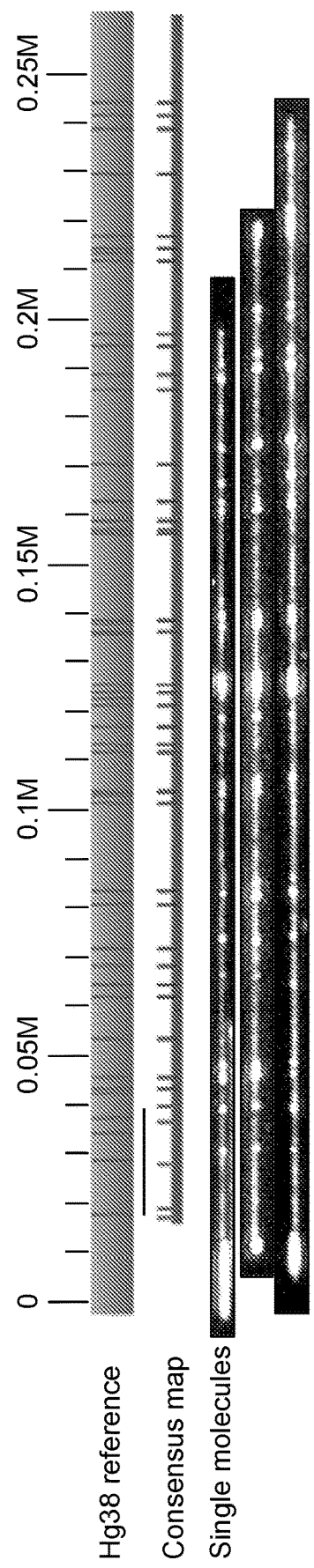
FIG. 3B is graph showing three color labeling results for chromosomes 12p of sample GM11832. The individual molecules were de novo assembled into the consensus maps which were mapped back to the hg38 reference. The lines on the consensus maps are Nt.BsPQI (CGTCTTC) sites that align to the corresponding reference site. Those that do not align with the reference are designated with a bar above the lines. A few of the single molecules that make up the consensus maps are shown (DNA backbone, labeled Nt.BsPQI sites (bright points all along backbone), and telomere (bright spots on left side)).

Further, the Cas9n fluorescent nick-labeling method was applied to a plasmid containing the HIV-1 genome. Multiple sgRNAs were designed and tested to target HIV-1 structural region (Gag, Pol, Env) to determine the most effective gRNA that labels the HIV-1 genome. The sites were correctly labeled with the expected distances between each sgRNA (FIG. 3B). However, the labeling efficiencies at each site of 36%, 58% and 44% from the left most label respectively, suggesting that labeling efficiency may be sequence- or region-dependent. It could also be the difference in labeling efficiency of sgRNA versus gRNA. The labeling efficiencies of the gRNAs were much higher than those achieved using sgRNAs.

Figure 3C:
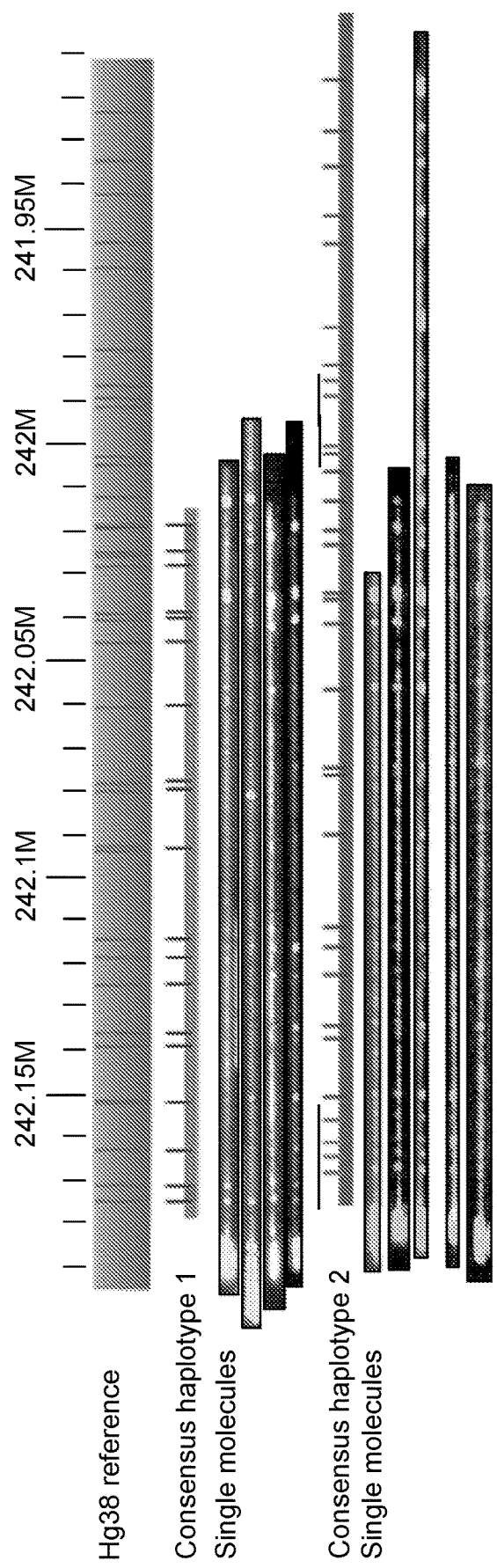
FIG. 3C is graph showing two color and three color consensus maps of both haplotypes and single molecules for chromosome 2q of sample IMR90-83. The individual molecules were de novo assembled into the consensus maps which were mapped back to the hg38 reference. The lines on the consensus maps are Nt.BsPQI (CGTCTTC) sites that align to the corresponding reference site. Those that do not align with the reference are designated with a bar above the lines. A few of the single molecules that make up the consensus maps are shown (DNA backbone, labeled Nt.BsPQI sites (bright points all along backbone), and telomere (bright spots on left side)).

In a third model system, a fosmid containing a subtelomeric segment of human 1q ending in 100 bases of $(TTAGGG)_n$ was used to test the Cas9n fluorescent nick-labeling. Four guide RNA probes were designed to target the $(TTAGGG)_n$ tract and three distinct loci on the subtelomere. The labeling pattern matched very closely with the positions of the gRNA seed sequences in the 1q reference sequence (FIG. 3C). However, the labeling efficiency was relatively lower for the telomere with 30%, while the labeling efficiency of subtelomeric markers were 95%, 79% and 99% respectively from the left most left label on 1q (FIG. 3C). This might be due to non-Watson-Crick pairings of the hexameric repeats, the high G+C content or the secondary structure of guide RNA probes targeting the $(TTAGGG)_n$ repeat.

EXAMPLE 3 the Two Color Genome Mapping with Cas9n Fluorescent Nick Labeling and Sequence-Motif Labeling After nicking with Cas9n D10A as previously described in Example 2, the sample was digested with RNAseA (190 ng/μL, QIAGEN®) at 37° C. for 20 min. After digestion, the sample was labeled with ATTO 532-dATP, dTGC (100 nM) and 2.5 units of DNA Taq Polymerase (NEB) in the presence of 1× Thermopol Buffer (NEB) at 72° C. for 1 h. The sample was treated with 1 unit of SAP (USB Products) and RNAseA (100 ng/μL) at 37° C. for 20 min and then 65.0 for 15 min. The nicks were repaired with 500 μM NAD+, 100 nM dNTPs and 20 kU of Taq DNA Ligase at 45° C. for 20 min. The sample was then treated with 6 mAU of QIAGEN Protease at 56° C. for 10 min and 70° C. for 15 min. The sample was dialyzed in TE on a 0.1 μm membrane (Millipore®) for 2 h. After dialysis, the sample was nicked with 10 units of Nt. BspQI (NEB) at 72° C. for 2 h. The nicked DNA was then labeled with 2.5 units of Taq DNA Polymerase (NEB), 0.1 μM ATTO-647 dUTP dAGC and 1× Thermopol Buffer (NEB) for 60 min at 72° C. The DNA backbone was stained with YOYO-1, and is shown in blue in all figures. The stained samples were loaded and imaged inside the nanochannels following the established protocol (See, Lam, E. T., et al. (2012). "Genome mapping on nanochannel arrays for structural variation analysis and sequence assembly." Nature Biotechnology 30(8): 771-776). The distances were calculated between spots using ImageJ. The histogram of the label distributions were plotted in Excel. If the pattern matched the predicted pattern we considered the labels as true positives. Missing labels were used for the calculation of labeling efficiency and the extra labels were used for calculating the false positive percentage.

Figure 4A:
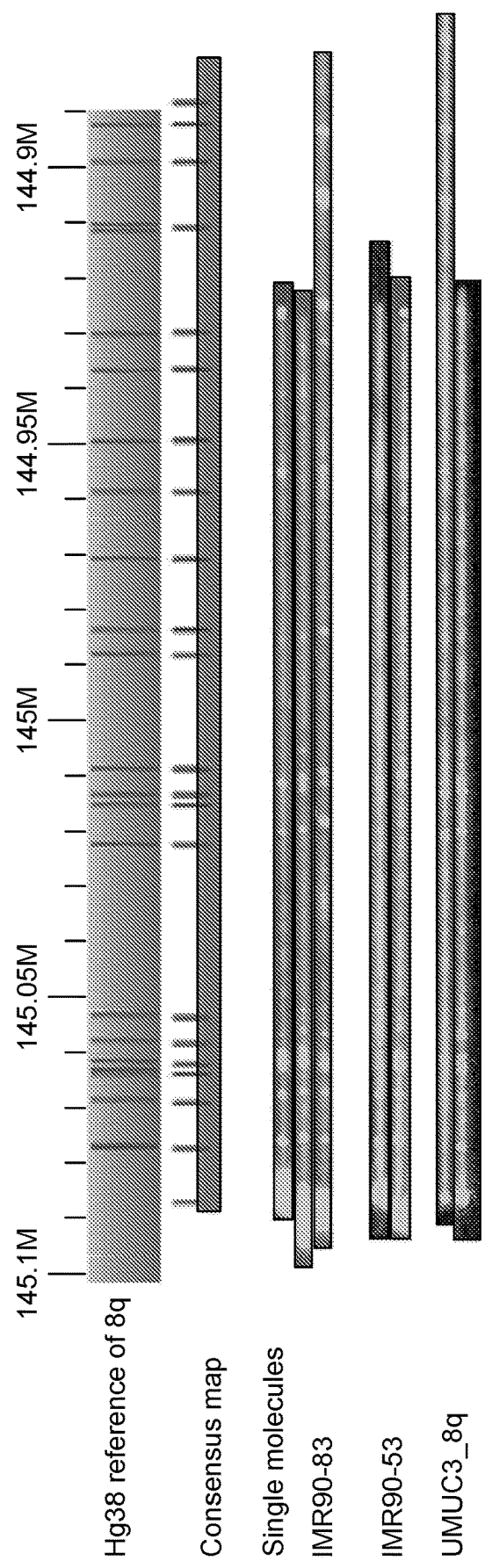
FIG. 4A is a graph of two color labeling results of chromosome 8q of IMR90 aging cell line at different population doublings and UMUC3 cancer cell line. The consensus map for all three samples is shown. The GCTCTTC motif labels that match the hg38 are the lines on the consensus map, except for the telomere label is represented on the consensus map as the leftmost line and not found on the hg38 reference.

The combination of Cas9n fluorescent nick-labeling with nicking endonuclease based sequence motif labeling was tested. This approach was designed to find wide applications in whole genome mapping of repetitive sequences as well as genotyping of structural variations and identification/mapping of viral integration sites. In FIG. 4A, the DUF1220 triplet repeats were first labeled with Cas9n fluorescent nick-labeling of red fluorescent nucleotides. These labeled DNA molecules were then globally nick-labeled with green nucleotides using Nt.BspQI to target the GCTCTTC motif. Twelve copies of DUF1220 triplets were detected spanning about 52 kb. Only the flanking regions of this 52 kb were shown to have the GCTCTTC motif, which can be mapped to reference genome to indicate the genomic locations of the DUF1220 triplet array. The histogram of the label distribution was shown in the bottom graph of FIG. 4A. Clearly, the combination of Cas9n fluorescent nick-labeling and nicking endonuclease sequence motif labeling, not only can detect the copy numbers of the DUF1220 triplets, but also can map the locations of the repeats.

Figure 4B:
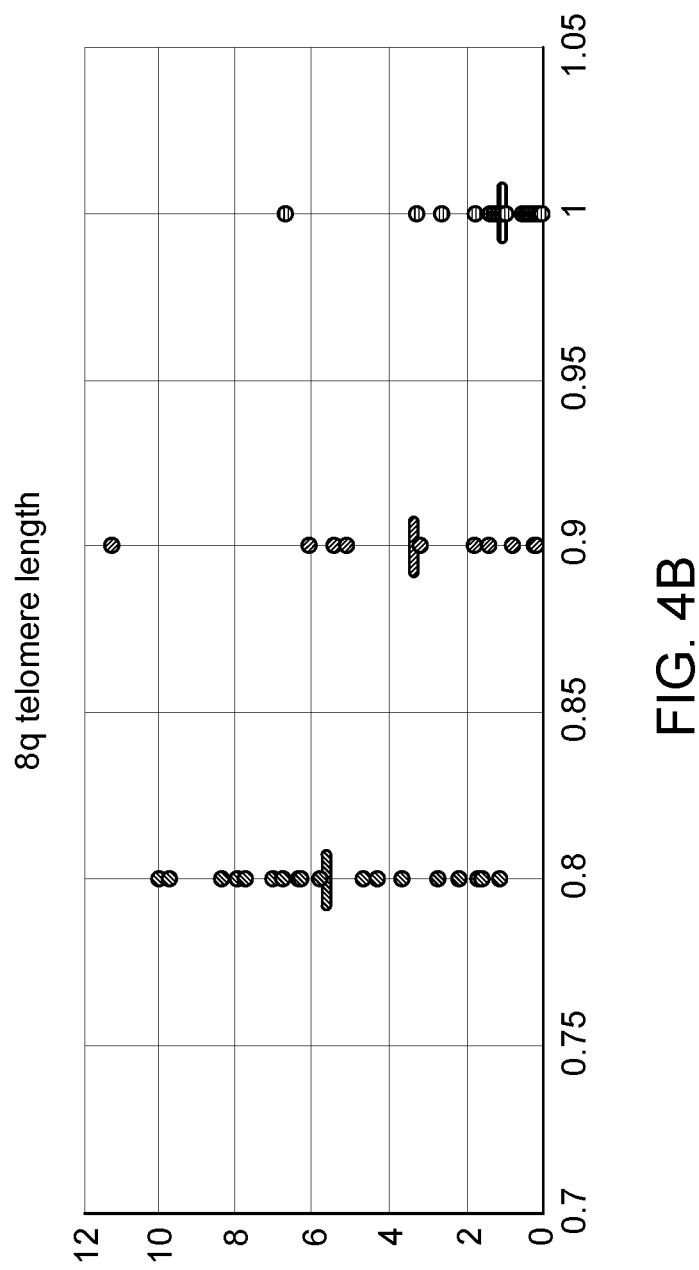
FIG. 4B is a graph of the telomere length measurement for chromosome 8q of IMR90-83 (PD 17), IMR90-53 (PD 45), UMUC3, and LnCap cells via two color labeling scheme. Each individual telomere is represented by a dot and the average telomere length is shown as a line.

The same approach was also applied to measure the telomere repeat length of a telomere-terminal fragment of chromosome 8q cloned in a fosmid. This fosmid carries 800 bp of the repetitive $(TTAGGG)_n$ sequence, which lacks motif nicking sites recognized by currently available nicking endonucleases and therefore cannot be labeled with current sequence-motif based methods. A gRNA specific for the telomere was designed. In FIG. 4B, the telomere was first labeled with Cas9n fluorescent nick-labeling of red fluorescent nucleotides. The labeled DNA molecules were then labeled with green nucleotides by Nt.BspQI nick-labeling to target the GCTCTTC motif. The telomere was correctly labeled on the end of the sequence. The length of this telomere region was determined by measuring the length of the red fluorophore region and the intensity of its fluorescence relative to known controls after imaging. Sequence motif labeling over extended subtelomere regions linked on single large DNA molecules to the Cas9n fluorescent nick-labeling $(TTAGGG)_n$ can be used to identify the specific subtelomere by comparison with genome-wide maps.

Cas9n fluorescent nick-labeling was used to create locus-specific and variant-specific barcodes. gRNAs were designed to create barcodes to distinguish individual subtelomeres linked on single molecules to $(TTAGGG)_n$ tracts (FIG. 5A, Chr 1q and Chr 11q) and to distinguish variant copies of highly similar subtelomeric segmental duplications (Chr 15q and Chr 12p) using the Cas9n sequence specific labeling methods. It has been suggested that the shortest telomere or a small subset of the shortest telomeres in a cell determines the onset of senescence, apoptosis or genome instability (Kaul, Z., et al. (2012). "Five dysfunctional telomeres predict onset of senescence in human cells." Embo Reports 13(1): 52-59; and Zou, Y., et al. (2004). "Does a sentinel or a subset of short telomeres determine replicative senescence?" Molecular Biology of the Cell 15(8): 3709-3718), the ability to systematically measure individual dysfunctionally short $(TTAGGG)_n$ tracts (rather than average telomere tract lengths in a sample as is typically measured currently) would provide important new high-resolution information on specific telomere functional status and identity at the single-molecule level. On the telomeric fosmids from Chr 15q and Chr 12p (FIG. 5A), Cas9n-gRNA directed nicks at two loci in a segmentally duplicated subtelomere region containing the WASH gene family (See, Linardopoulou, E. V., et al. (2007). "Human subtelomeric WASH genes encode a new subclass of the WASP family." PLoS Genet 3(12): e237) were labeled in red. The same pair of gRNAs generated signals separated by 5.87 kb on the 15q fosmid and 7.5 kb on Chr 12p fosmid, as predicted by the reference sequences of these two highly similar but structurally non-identical regions. The patterns generated by three target-specific gRNAs on Chr1q and two gRNAs on 11q were unique, easily distinguishable from each other and from both of the WASH gene-related patterns, and corresponded exactly to what was expected from their respective reference sequences. These experiments indicate that specific gRNAs were pooled to generate multiple specific nicks that, when labeled, can create custom barcodes predicted precisely by the respective reference sequences.

Figure 5B:
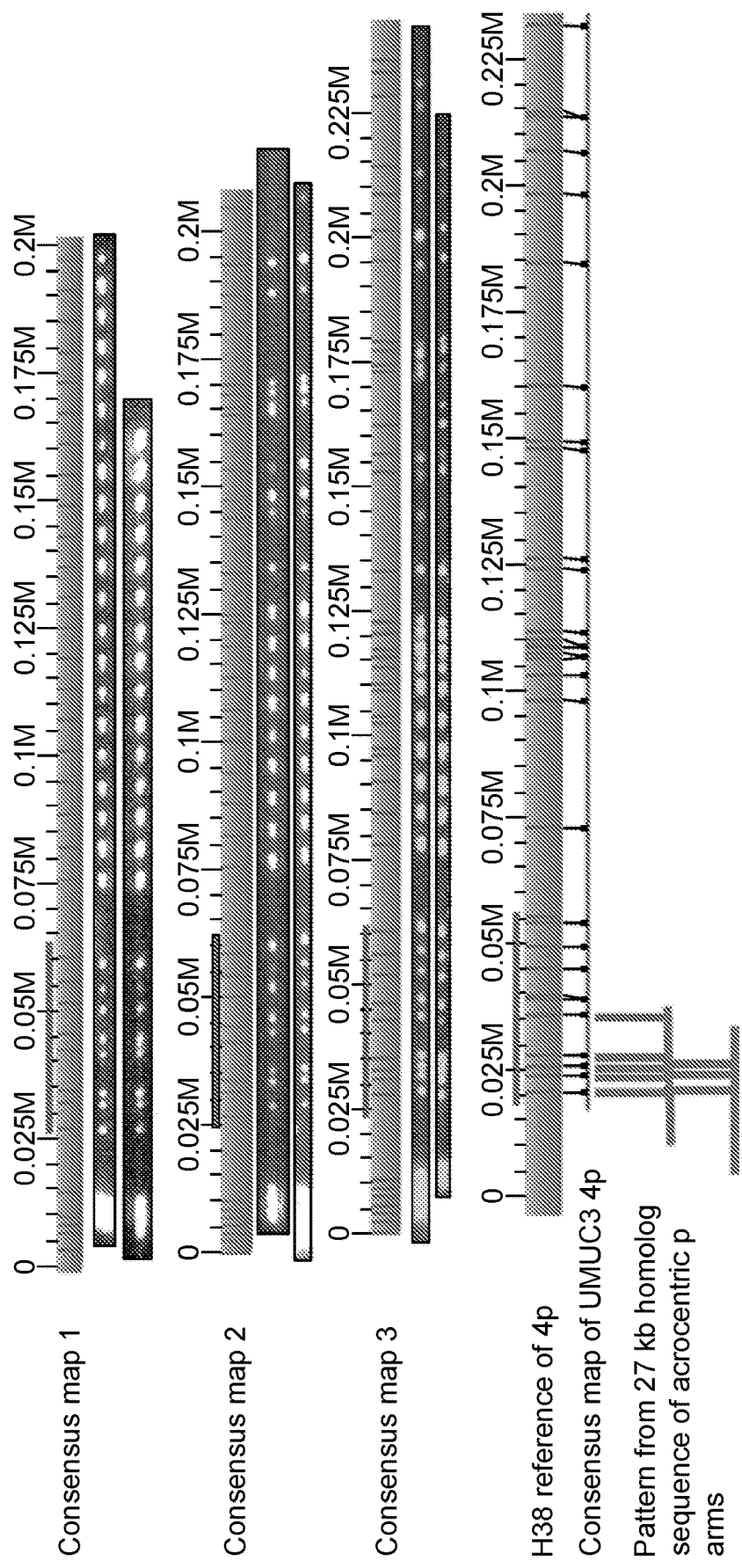
FIG. 5B is a graph of the three consensus maps which could not be mapped to the hg38 reference. They were also found to have an extra intense telometric label at one end.

FIG. 5B shows the results of experiments combining the Cas9n fluorescent nick-labeling and nicking endonuclease sequence motif labeling to map Alu elements in the human genome. A gRNA was designed to target 280 000 Alu sites out of one million copies. Typical genomic DNA molecules were imaged and shown in FIG. 5B. One 180 kb molecule displayed dense Alu elements with only two GCTCTTC motifs. Another DNA molecule showed dense Alu elements with two GCTCTTC motifs. The combined information can be used to map the DNA molecules to the reference genome and profile the distribution of Alu elements on the whole genome scale.

EXAMPLE 4

Preparation of DNA Samples and Guide RNA

*Homo sapiens* transitional cell carcinoma UMUC-3, lung fibroblast IMR-90 and GM11832 were cultured and maintained at 37° C. in a 5% $CO_2$ humidified incubator.

To extract DNA with high molecular weight, mammalian cells were embedded in gel plugs and High Molecular Weight DNA was purified as described in a commercial large DNA purification kit (BioRad #170-3592). Plugs were incubated with lysis buffer and proteinase K for four hours at 50° C. The plugs were washed and then solubilized with GELase™ (Epicentre®). The purified DNA was subjected to 2.5 hours of drop-dialysis. It was quantified using Quant-iT™ dsDNA Assay Kit (Life Technology®), and the quality was assessed using pulsed-field gel electrophoresis.

To prepare the guide RNAs, the seed sequence of 20 nucleotides complementary to the 3'-5' strand of the telomere (UUAGGGUUAGGGUUAGGGUU, SEQ ID NO: 1) was designed via a gRNA design tool (Feng Lab CRISPR Design Web Tool at crispr.mit.edu.). This seed sequence was incorporated into the crRNA. The crRNA and the universal tracrRNA, were synthesized by GE Dharmacon. The telomere gRNA was created by pre-incubating the tracrRNA (0.1 nmol) and crRNA (0.1 nmol) on ice for 30 minutes.

EXAMPLE 5

CRISPR-Cas9 Labeling of Human Genomic DNA for Telomere Length Measurement and Haplotype Determination To perform the two color labeling scheme, the gRNA (2.5 µM) was incubated with 200 ng of Cas9 D10A (LabOmics), 1× NEBuffer 3 (New England BioLabs, NEB), and 1× BSA (NEB) at 37° C. for 15 minutes. The DNA (300 ng) and 5U of Nt.BspQI (NEB) were added to the mixture and incubated at 37° C. for 60 minutes. The nicked DNA was labeled with 5U of Taq DNA Polymerase (NEB), 1× Green Labeling Mix (BioNano Genomics), and 1× Thermopol Buffer (NEB) at 72° C. for 60 minutes. The nicks were repaired with 20kU of Taq DNA Ligase (NEB), 1 mM NAD+(NEB), 100 nM dNTPs, and 1× Thermopol Buffer (NEB) at 37° C. for 30 minutes.

To perform the three color labeling scheme, the DNA (300 ng) was first nicked with 5U of Nt.BspQI (NEB) in 1× NEBuffer 3 (NEB) at 37° C. for 2 hours. The nicked DNA was then labeled with 5U of DNA Taq Polymerase (NEB), 1× IrysPrep Labeling Mix Red (BioNano Genomics), and 1× NEBuffer 3.1 (NEB) at 72° C. for 60 minutes. The sample was treated with 0.3U of SAP (USB Products) at 37° C. for 10 minutes and then 65.0 for 5 minutes. The gRNA (2.5 µM) was incubated with 200 ng of Cas9 D10A (LabOmics), 1× NEBuffer 3 (NEB), and 1× BSA (NEB) at 37° C. for 15 minutes. The red-labeled sample was then added to the reaction and incubated at 37° C. for 1 hour. The Cas9 D10A nicks were labeled with 2.5U of Taq DNA Polymerase (NEB), 100 nM ATT0532-dUTP dAGC, and 1× NEBuffer 3.1 (NEB) at 72° C. for 60 minutes. The nicks were repaired with 20kU of Taq DNA Ligase (NEB), 1 mM NAD+(NEB), 100 nM dNTPs, and 1× NEBuffer 3.1 (NEB) at 37° C. for 30 minutes.

After nick-labeling with either the two or three color schemes, the samples were treated with 6 mAU of QIAGEN Protease at 56° C. for 30 minutes and the reaction was stopped with 1 µL of IrysPrep Stop Solution (BioNano Genomics). The DNA backbone was stained with 333 nM YOYO-1 (Invitrogen) and is shown in blue in all figures. The stained samples were loaded and imaged inside the nanochannels following the established protocol (Lam, E. T., et al. (2012). "Genome mapping on nanochannel arrays for structural variation analysis and sequence assembly." Nat Biotechnol 30(8): 771-776).

Single-molecule maps were assembled de novo into consensus maps using software tools developed at BioNano Genomics, specifically RefAligner and Assembler (Mak, K. S., et al. (2016). "Defining a standard set of patient-centred outcomes for lung cancer." Eur Respir J 48(3): 852-860). Briefly, the assembler is a custom implementation of the overlap-layout-consensus paradigm with a maximum likelihood model. An overlap graph was generated based on pairwise comparison of all molecules as input. Redundant and spurious edges were removed. The assembler outputs the longest path in the graph and consensus maps were derived. Consensus maps were further refined by mapping single molecule maps to the consensus maps and label positions were recalculated. Refined consensus maps were extended by mapping single molecules to the ends of the consensus and calculating label positions beyond the initial maps. After merging of overlapping maps, a final set of consensus maps was output and used for subsequent analysis.

The molecules were mapped to hg38 and the ends of the individual chromosomes were analyzed. The telomere label was the intense additional label not found in the reference. The intensity of this label was measured and compared to the background intensity. This was then converted to base pairs by comparing to a standard curve (data not shown).

To confirm the subtelomeric sequence motif labeling is able to differentiate individual chromosomes and the telomeric labeling is sufficient for telomere length measurement, the mapping results from 100 human genomes demonstrated that the Nt.BspQI (CGTCTTC) motif labeling successfully differentiated chromosomes. The SREs of 1p, 5q, and 8p are shown in FIG. 2A. The three chromosome arms share several SREs which have greater than 90% identity shared by copies (Stong, N., et al. (2014). "Subtelomeric CTCF and cohesin binding site organization using improved subtelomere assemblies and a novel annotation pipeline." Genome Res 24(6): 1039-1050). The mapping results clearly showed that Nt.BsPQI nickase based whole genome mapping can distinguish these closely related SREs. Only a 150 kb region was needed to differentiate these three highly similar SRE chromosomes from each other.

Figure 2B:
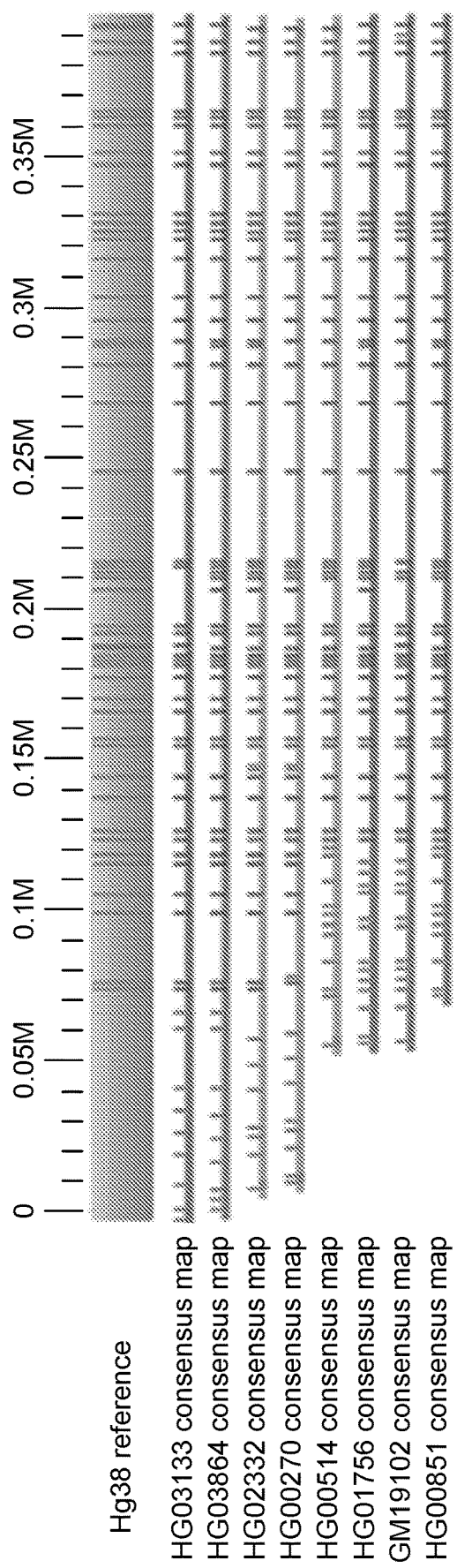
FIG. 2B is a graph of the labeling results of chromosomes 6p. The consensus maps after de novo assembly and references are shown as light bars and the dark bars within these indicate the Nt.BspQI nick-label sites. The single molecules that comprise the respective consensus map are the lines shown directly below. The labels on the single molecules that align with the hg38 reference are dark and those that do not align are light. The major haplotypes of chromosome 6p were detected from 8 individuals.
Figure 2C:
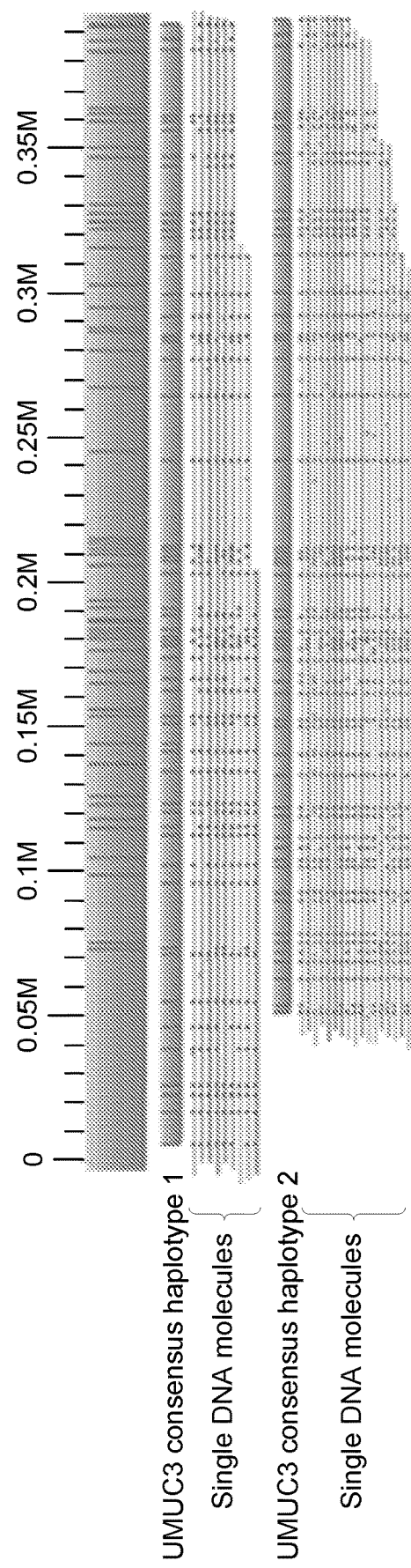
FIG. 2C is a graph of the labeling results of chromosomes 6p in UMUC3 cancer cells. The consensus maps after de novo assembly and references are shown as light bars and the dark bars within these indicate the Nt.BspQI nick-label sites. The single molecules that comprise the respective consensus map are the lines shown directly below. The labels on the single molecules that align with the hg38 reference are dark and those that do not align are light. The two distinct haplotypes of the cancer genome UMUC3 for chromosome 6p were detected.

The nick-labeling whole genome mapping method can also detect haplotypes. F8 major haplotypes of chromosome 6p were detected from 8 individuals (FIG. 2B). The consensus maps each contained non-aligned labels to the hg38 reference (light blue lines) and differ from one another. There were two distinct haplotypes of the cancer genome UMUC3 and therefore was heterozygous at 6p (FIG. 2C). Then, whole mapping results over 100 human genomes were generated and the vast majority of the subtelomeric SREs could be distinguished based on the Nt.BsPQI nicking patterns.

After confirming the subtelomeric sequence motif labeling was able to differentiate chromosomes, the CRISPR-Cas9 telomeric labeling was tested with a circular fosmid with sequences cloned from the human chromosome arm 8q, containing 800 bp telomeric repeats. There was no fluorescent labeling of the telomeric repeats (TTAGGG) without the presence of either Cas9n or gRNA (data not shown). The fluorescent labeling of telomeric repeats was detected only when both Cas9n and gRNA were present in the reaction. The Cas9n (TTAGGG) and Nt.BsPQI (CGTCTTC) were further combined to nick-label the fosmid at the same time. After linearization with NotI enzyme, the Nt.BsPQI labeling pattern of the fosmid matched the reference sequences and the telomeric labeling was always at the telomeric repeat end of the molecules.

The subtelomeric sequence motif labeling differentiates individual chromosomes and the total intensity of the telomere labeling was used to calculate the telomere length and the assay was tested on human genomic DNA and several different cell lines. In the first application, the three color scheme was tested on human genomic sample GM11832. The results for chromosomes 3p and 12p are shown in FIGS. 3A and 3B respectively. Again, this result shows that the subtelomeric sequence motif labeling differentiated individual chromosomes and the telomere was labeled which can be used to calculate the telomere length.

The two color scheme was then tested with the IMR90 cell line. The single molecules produced from both the two-color and three-color schemes generated the same consensus maps. The telomere length assay also identified haplotypes and the consensus maps of both haplotypes and single molecules for chromosome 2q of sample IMR90-83 were acquired (FIG. 3C). The two color scheme generates longer DNA molecules for mapping, was a simpler experimental procedure, and involved much less imaging time with 2/3 of the data storage requirements.

Furthermore, the two color labeling scheme was applied to identify individual telomere lengths on the IMR90 aging cell line at different population doublings and the UMUC3 and LnCap cancer cell lines. The typical results for chromosome 8q are shown in FIG. 4. The UMUC3 telomere was found to be the shortest when compared to the IMR90 samples. IMR90-83 with a population doubling (PD) 17 had longer telomeres than the later passaged IMR90-53 PD45.

The specific tagging of telomeres is a very powerful tool to extract individual DNA molecules containing telomere repeats, which can be used to correct reference assembly or discover new subtelomeric structures. For all the genomes mapped, the subtelomeric region 0-500 kb of chromosome 1p was constantly missing. However, all the single DNA molecules used to form the consensus map to 600 kb downstream, all contain intense Cas9n end labels (two color labeling scheme) and intense red labels (three color labeling scheme) (FIG. 5A). This result indicates that 0-600 kb of the HG38 is not correct and should be deleted from the reference assembly. In addition, five consensus maps, which cannot be mapped to the Hg38 reference, were found to have an extra intense label at one end (FIG. 5B).

Figure 5C:
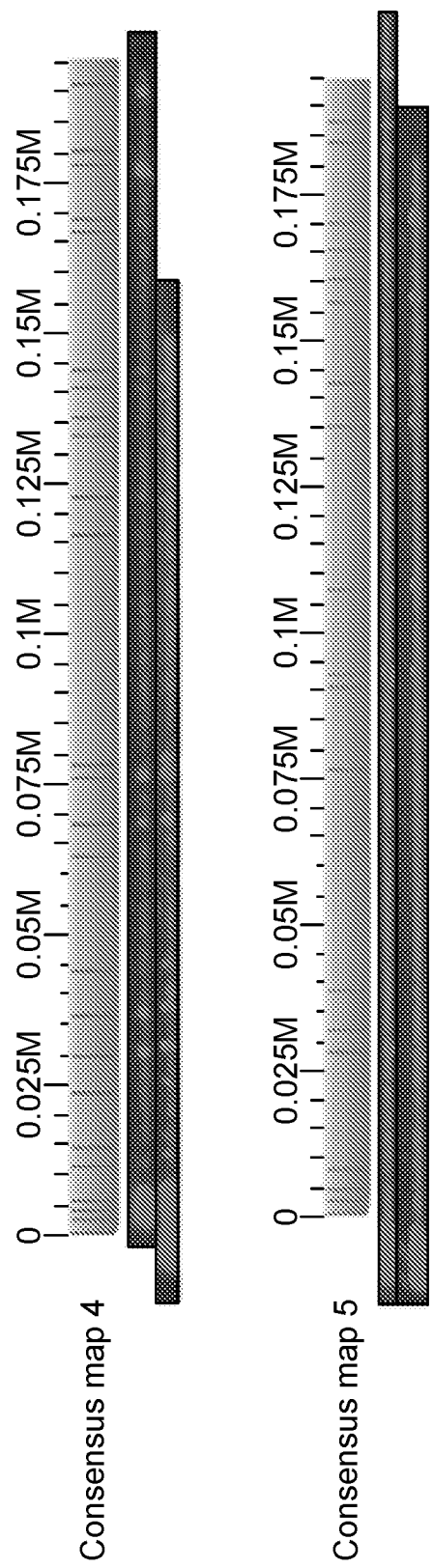
FIG. 5C is a graph of the two consensus maps which could not be mapped to the hg38 reference. They were also found to have an extra intense telometric label at one end.

Consensus maps 1, 2, and 3 shared a 40 kb conserved pattern, marked as the red bars in FIG. 5B. This pattern is similar to the pattern of chromosome 4p of HG38 from 25 kb to 65 kb. This region of consensus map 3 is slightly different than consensus maps 1 and 2. Two 27 kb homolog sequences have been sequenced from these acrocentric chromosomes, which share the similar patterns as with above consensus maps. Taken together with the telomeric labels at the end of DNA molecules, it is strongly suggested these three patterns belong to some of the 5 unknown acrocentric chromosomes ends 13p, 14p, 15p, 21p and 22p. Interestingly, they all have 7 kb repetitive sequence units following this 40 kb conserved pattern. Consensus map 1 has the longest 7 kb repeats over 140 kb, which made the sequences assembly impossible with current sequencing technologies. Based on these patterns, we located more unaligned consensus maps with the same patterns from other genome mapping results with some over 700 kb long (data not shown). The other two unaligned consensus maps with possible telomeric labels are shown in FIG. 5C.

Each person has two copies of all chromosomes, except the sex chromosomes in males. For each SNP, the combination of alleles a person has is called a genotype. The alleles of nearby SNPs on a single chromosome are correlated. A sequence of consecutive alleles on a particular chromosome is known as a haplotype. Currently, there is no good way to obtain haplotype over long distance >10Kb). The haplotypes are not limited to just SNP mutation, any human genetic marker can be used to define haplotypes.

EXAMPLE 6

Figure 6:
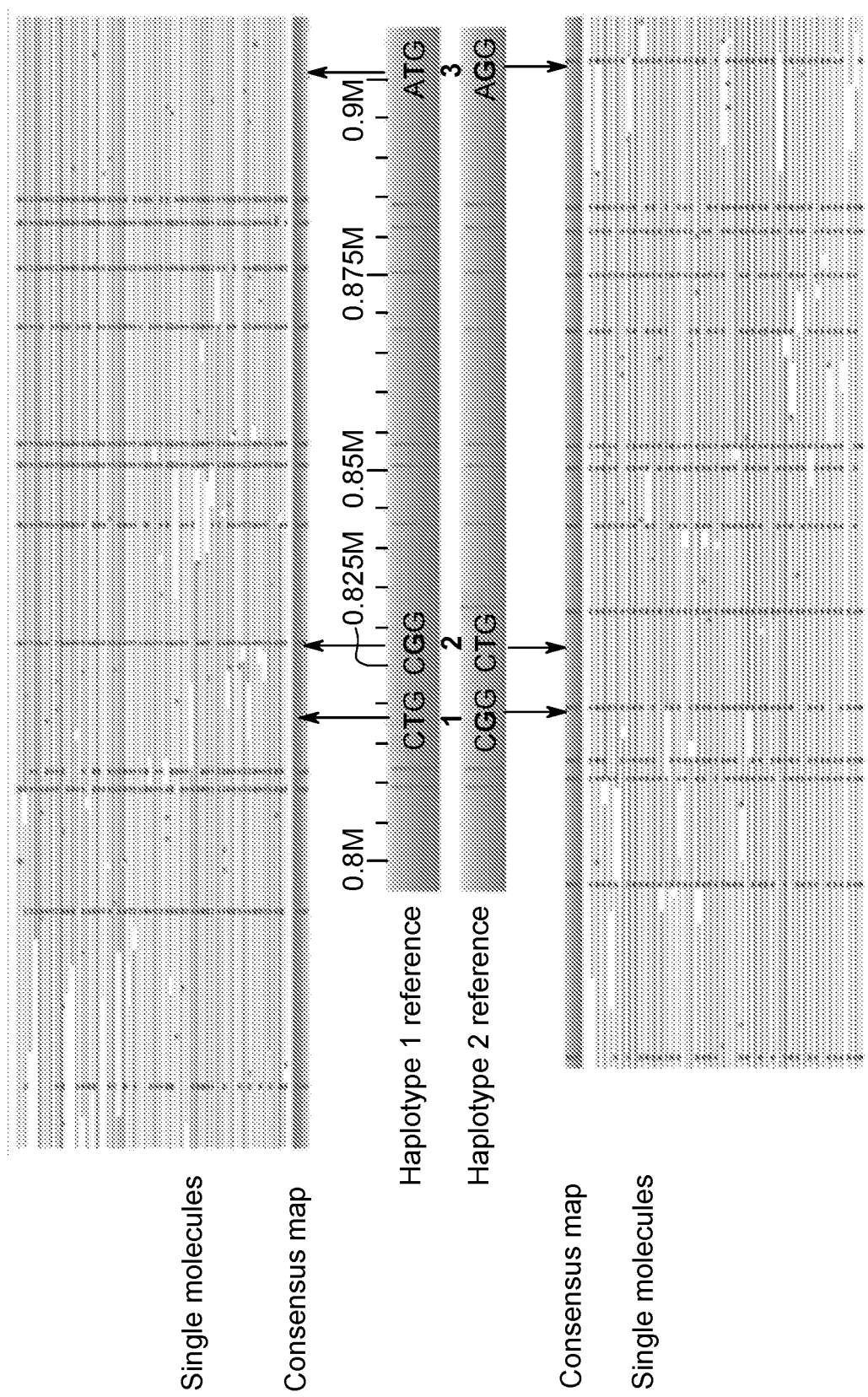
FIG. 6 is a graph of the two color labeling results for haplotype determination. The individual molecules were de novo assembled into the consensus maps which were mapped back to the reference (grey bars in the center). The dark lines on the consensus maps are the nicking sites that align to the corresponding reference site. Those that do not align with the reference are designated with light lines.

Using CRISPR-Cas9 System to Identify Individual SNP Alleles, Construct Long Distance Haplotypes, and Tag Specific Genomic Region of Interest A computational analysis of whole genomes sequenced by the 1000 genomes project was performed. On average, the density of heterozygous PAM-SNPs was kb/site and there were about 220,000 heterozygous PAM SNPs, in which one of the alleles is in the Cas9-required GG motif. In addition, the density of heterozygous Indel is 50 kb/site and there were 40,000 heterozygous Indels (>4 bp) within potential CRISPR-Cas9 recognition sequences (20 bp+NGG). The genomic density of these sites was ideal to generate long distance haplotypes, as our singe molecules were all longer than 180 kb. FIG. 6 shows a 100 kb region of two different haplotypes based on nicking motif mapping. Due to a single allele mutation at "A" locus (within the Nt.BspQI sequence motif) of haplotype 1, the Nt.BspQI nicking enzyme was unable to nick-label this particular site of haplotype 1. Then three PAM SNPs were selected at loci 1, 2 and 3. At locus "1" (AACCATTCAAACGGCGATTGCG/TG, SEQ ID NO: 17), haplotype 2 had the perfect CGG PAM sequence, while the haplotype 1 had CTG sequence at its PAM locus. Clearly, haplotype 2 had an extra label after CRISPR-Cas9 labeling, whereas haplotype 1 was not labeled at this site at all. Haplotype 1 had the perfect PAM sequence (CGG vs. CTG) at locus "2" and was labeled there. Haplotype 2 with perfect PAM sequence at locus 3 (AGG vs. ATG) was labeled. So for these three SNPS the haplotype can clearly be established over this 100 kb region as TGT of haplotype 1 and GTG for haplotype 2. This approach is particularly useful in defining haplotype-linked telomere lengths of interest and tracking them efficiently in large sample sets (e.g., case control studies).

Figure 7A:
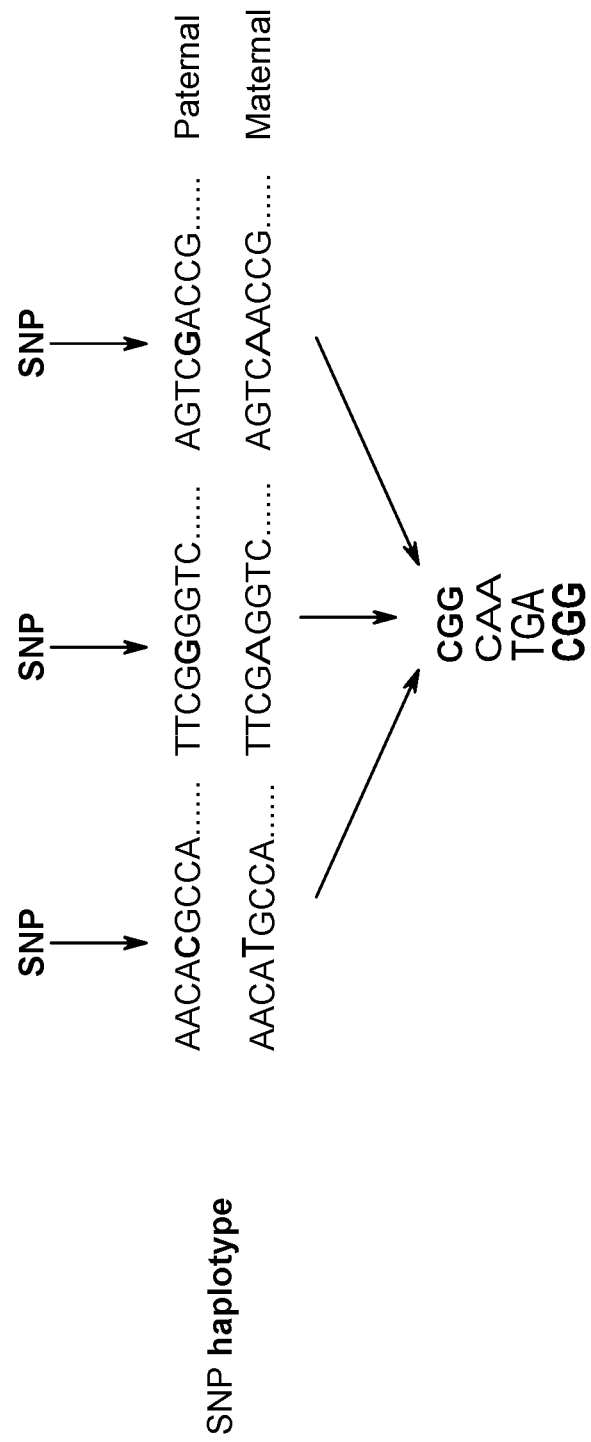
FIG. 7A is a graph showing that haplotypes were determined via SNP at different loci of paternal and maternal samples by CRISPR-Cas9 labeling. Some candidates of nicking sites are listed below the sequences.

In an example shown in FIG. 7A, SNP was recognized and detected via CRISPR-Cas9 labeling. There were three recognition sites in the sequences listed and thus, the paternal SNP haplotype was identified as CGG while the corresponding maternal one as TAA. Candidates of potential recognition sites are available and listed in the bottom of panel A.

In an example shown in FIG. 7B, Indels were recognized and detected via CRISPR-Cas9 labeling. SNP haplotypes were incorporated as well to generate specific barcode patterns in order to differentiate the alleles.

Figure 7C:
FIG. 7C is a schematic graph illustrating both three color haplotype labeling schemes via the Cas9 D10A (Cas9n) directed by the gRNA and Nt.BspQI globally nicking the GCTCTTC motif. The motif-dependent Nt.BspQI generated nicks which were then labeled with green fluorescently labeled nucleotides and the nicks generated by CRISPR-Cas9 were labeled with red fluorescently labeled nucleotides. The sequences displayed are labeled in descending order as SEQ ID NOs: 24-27, 1, 30, and 31.

In another example shown in FIG. 7C, the motif-dependent Nt.BspQI nicking enzyme was able to nick-label two sites in both paternal and maternal alleles. On the other hand, the 3 bp deletions in the paternal DNA could be revealed by positive fluorescent signal via the CRISPR-Cas9 labeling in the maternal samples.

Figure 7D:
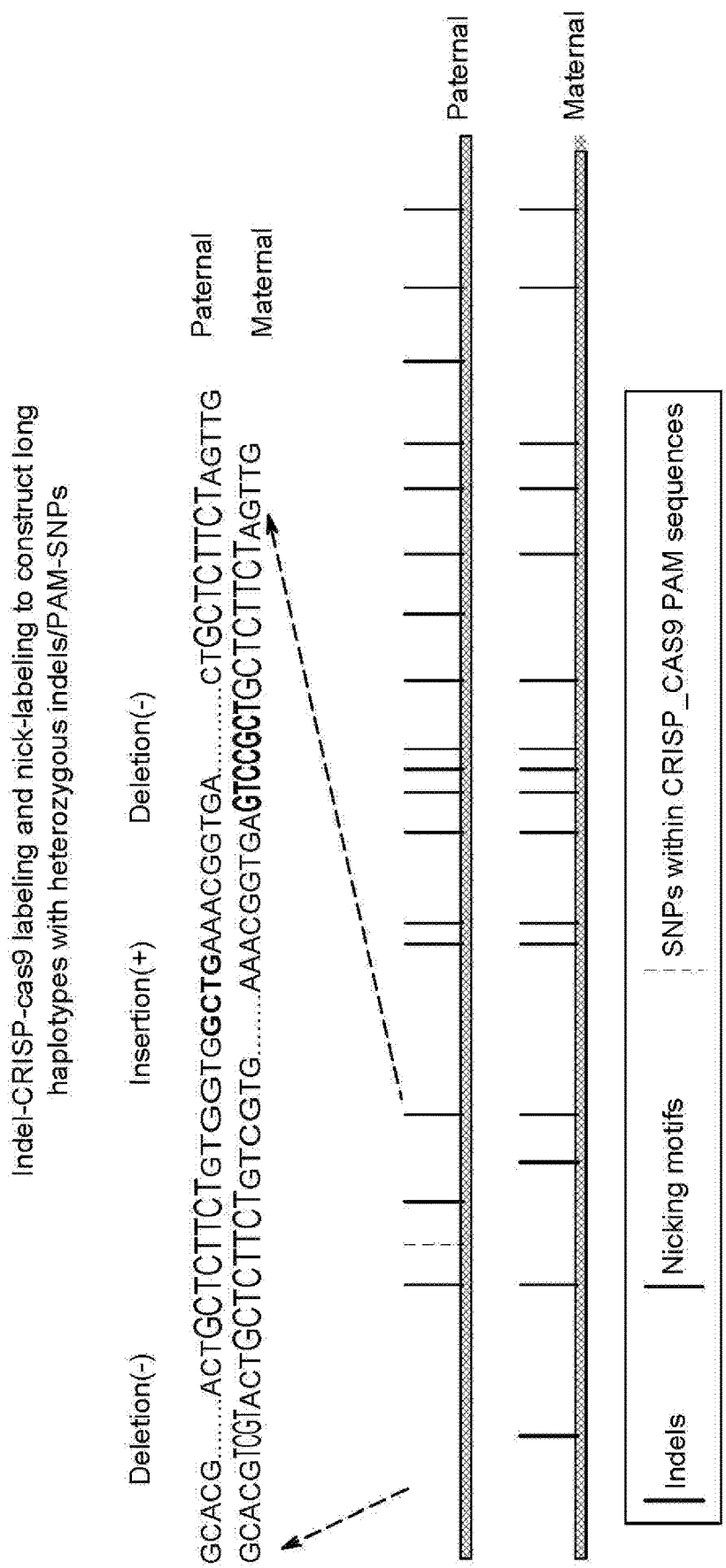
FIG. 7D is a graph showing one example of determining parental haplotypes. The motif-dependent Nt.BspQI generated nicks were labeled (shown in taller text in the consensus map). The labelled nicks generated by CRISPR-Cas9 due to Indels are shown in larger bolded text. The SNPs within CRISP-Cas9 PAM sequences are shown in as wider text. Paternal sequence is SEQ ID NO: 32. Maternal sequence is SEQ ID NO: 33.

In a further example shown in FIG. 7D, while the nicking motifs were presented in both paternal and maternal sequences, the CRISPR-Cas9 labeling identified both the Indels and SNPs within CRISP-Cas9 PAM sequences (TGG) and provided specific barcode patterns that could differentiate the alleles.

Considered density of heterozygous PAM-SNPs/Indels (for example, Sample HG0100 has about 3000 heterozygous Indels and 9000 PAM-SNPs in Chromosome 6), a haplotype with the density around 14 kb is constructed, which is perfect for most genetic research and clinical testing.

EXAMPLE 7

Applications: Using CRISPR-Cas9 System for Whole-Genome Mapping and/or Labeling of Specific Genomic Regions of Interest The barcoding scheme is initialized via the customer-chosen design of a 20 base pair (bp) seed sequence, which is immediately flanked by a PAM sequence, represented by the trinucleotide, NGG. In other words, the target for the probe is 23 bp total, with the first 20 bp designed by the user and the remaining NGG within the template genome itself. For whole-genome or specifically-labeled genomic regions, frequent kmers with varying repetitive densities are targeted. In this strategy, precise control is retained over the frequency of targets, thus labeling density, enabling comprehensive mapping of an entire genome or any region of a genome. In the case of design using kmers, the focus is on the seed sequence, which is the 10-12 bp immediately adjacent to the PAM motif. Based on this sequence, it is possible to design the gRNA to comprise different frequencies (e.g., 100,000 or 300,000 sites). Further, the design algorithm can screen several designed probe sequences and choose the gRNA(s) that heavily discriminate against changing any one of the bases. In preliminary whole-genome mapping work, it was found that less than 10% of the designed probe target sequences have a single base mismatch in the human genome, which can be discriminated with CRISPR-Cas9 labeling. Thus, a less than 1% false positive rate was achieved, while maintaining over 90% labeling efficiency.

Given the flexibility of the design parameters, this method may be used on any genome and any regions of a particular genome, which is not possible with the current nickase-based approach. Further, the approach circumvents common complications from commercial nicking endonucleases, such as fragile sites and sparsely-targeted regions.

EXAMPLE 8

Applications: Using CRISPR-Cas9 System to Differentiate Single Base/Allele for Haplotyping (Haplotyping gRNAs)

A second application of the gRNA design approach consists of single base or allele haplotyping. In this process, identify high minor allele frequency (MAF) heterozygous SNPs are identified using the publicly-available 1000 Genomes Project sequences. The PAM requirement for target binding and labeling was exploited by finding heterozygous SNPs with high MAFs in the first G of the PAM NGG. Heterozygous SNPs in the second G of PAM were avoided, due to the possibility of additional adjacent Gs which may decrease target precision and/or frequency. In addition, the PAM sequence GGG was avoided, for the same reasons outlined. Initially, discrimination of 2 pooled strains of *Haemophilus* influenza was completed, Rd SpcR, Hi375 StrR, and 86-028NP NovR NalR, which mimicked a diploid organism, in that mapping and labeling was performed blind to the origins of molecules from the respective strains. After mapping and labeling, the locations of known SNPs in each organism were used to identify which molecules derived from which strain. Over 99% of the molecules that were expected to contain an extra Cas9-derived label, did so, as did over 99% of molecules expected to not contain a label. To apply the MAF threshold, this approach was successfully applied to chromosome arm 6p of human genome GM2603. A location nearest the beginning of the chromosome around position 230,973 bp and 254,170 bp were identified, which 2 gRNAs target in tandem in these 2 regions with MAF>=0.4 and designed 2 gRNAs (CCAAGGCCGAC-AAAGTCCAG, SEQ ID NO: 18; AAAACCAAGAA-TCCTTTTGT, SEQ ID NO: 19). The gRNAs will target and label roughly 80% of the mapped molecules, discriminating the 2 haplotypes of the individual.

EXAMPLE 9

Applications: Increase the Fluorescent Signal Targeting Repetitive Sequences

The targeting of consensus 20 bp sequences in the most common repetitive sequences interspersed in the human genome were leveraged to increase the frequency of fluorescent signals. Keeping all gRNA design specifications the same as described in the previous 2 approaches, the design was successfully applied to target a 20 bp consensus (GCC-TATAATCCCAGCAC, SEQ ID NO: 20) in the Alu element. This mobile element has an estimated presence of over 1 million copies in the human genome and our gRNA targets ~300,000 of these sites. To demonstrate the control of the gRNA in labeling efficiency, experimentation was done with altering seed bases to measure the effects of targeting frequency. It was found that changing any one of the seed bases dramatically decreases the frequency of targeting from 300,000 sites to just 4,000 sites, a 75-fold decrease. This experiment illustrates the importance of correct design of gRNA sequences for precision and control of any of the labeling methods. Further, using this design feature, it is possible to tune the gRNA according different genomes. Finally, it is possible to use tandem either one or multiple gRNAs targeted to close locations to greatly increase the intensity of a fluorescent signal in a specific genomic region. This approach was successfully applied to chromosome 8q, in which we identified 3 gRNAs that target locations within 800 bp of one another (tccagacttatgccactgagagg: 145033016, SEQ ID NO: 21; taaataccacaaggaaatcttgg: 145033349, SEQ ID NO: 22; and acccctattcctttaaaagccagg: 145033797, SEQ ID NO: 23). The use of these gRNAs enabled the identification of subtelomeres in chromosome 8q for further analyses.

All publications cited in this specification are incorporated herein by reference as well as U.S. Provisional Patent Application No. 62/410,322, filed Oct. 19, 2016, and 62/410,324, filed Oct. 19, 2016, which are incorporated by reference herein. The publication McCaffrey et al, Nucleic Acids Research, 2015, 44(2):e11 doi: 10.1093/nar/gkv878 is specifically incorporated herein by reference in its entirety. While the invention has been described with reference to particularly preferred embodiments, it will be appreciated that modifications can be made without departing from the spirit of the invention.

EMBODIMENTS

1. A method of detecting the length of an individual telomere, the method comprising:
a) contacting genomic DNA with a guide RNA having a portion complementary to the telomere repeat sequence in the genomic DNA and with Cas9 nickase to produce a single-strand break in the genomic DNA at the telomere repeat sequence;
b) contacting the nicked DNA with a polymerase and fluorescently labeled nucleotide, wherein the fluorescently labeled nucleotide is incorporated into the nicked DNA at the telomere repeat sequence;
c) contacting the genomic DNA with a second nicking endonuclease which is specific for a sequence motif in the genomic DNA thereby producing a second nick in the genomic DNA at the motif sequence;
d) contacting the nicked DNA with a polymerase and second fluorescently labeled nucleotide of the same color or different color, wherein the second fluorescently labeled nucleotide is incorporated into the nicked DNA at the motif sequence location; and
e) detecting the length of the telomere by measuring the fluorescence of first fluorescently labeled nucleotide at the telomere repeat location, wherein the fluorescently labeled motif sequences are used as a barcode to identify the chromosome.

2. A method of detecting the length of an individual telomere, the method comprising: (two color method-motif nicking)

a) contacting genomic DNA with a guide RNA having a portion complementary to the telomere repeat sequence in the genomic DNA and with Cas9 nickase to produce a single-strand break in the genomic DNA at the telomere repeat sequence;

b) contacting the genomic DNA with a second nicking endonuclease which is specific for a sequence motif in the genomic DNA thereby producing a second nick in the genomic DNA at the motif sequence, c) contacting the nicked DNA with a polymerase and fluorescently labeled nucleotide, wherein the fluorescently labeled nucleotide is incorporated into the nicked DNA at the telomere repeat sequence and at the motif sequence; and d) detecting the length of the telomere by measuring the fluorescence of first fluorescently labeled nucleotide at the telomere repeat location, wherein the fluorescently labeled motif sequences are used as a barcode to identify the chromosome.

3. A method of detecting the length of an individual telomere, the method comprising:

a) contacting genomic DNA with a guide RNA having a portion complementary to the telomere repeat sequence in the genomic DNA and with Cas9 nickase to produce a single-strand break in the genomic DNA at the telomere repeat sequence;

b) contacting the nicked DNA with a polymerase and fluorescently labeled nucleotide, wherein the fluorescently labeled nucleotide is incorporated into the nicked DNA at the telomere repeat sequence;

c) contacting the genomic DNA with a second guide RNA having a portion complementary to a sequence in the subtelomeric region of the genomic DNA and with Cas9 nickase to produce a single-strand break in the genomic DNA at the subtelomeric sequence, d) contacting the nicked DNA with a polymerase and second fluorescently labeled nucleotide, wherein the second fluorescently labeled nucleotide is incorporated into the nicked DNA at the subtelomeric sequence location; and e) detecting the length of the telomere by measuring the fluorescence of first fluorescently labeled nucleotide at the telomere repeat location, wherein the fluorescently labeled subtelomeric sequence is used as a barcode to identify the chromosome.

4. A method of detecting the length of an individual telomere, the method comprising: (two color method-subtelomere nicking)

a) contacting genomic DNA with a guide RNA having a portion complementary to the telomere repeat sequence in the genomic DNA and with Cas9 nickase to produce a single-strand break in the genomic DNA at the telomere repeat sequence;

b) contacting the genomic DNA with a second guide RNA having a portion complementary to a sequence in the subtelomeric region of the genomic DNA and with Cas9 nickase to produce a single-strand break in the genomic DNA at the subtelomeric sequence, c) contacting the nicked DNA with a polymerase and fluorescently labeled nucleotide, wherein the fluorescently labeled nucleotide is incorporated into the nicked DNA at the telomere repeat sequence and at the subtelomeric sequence; and d) detecting the length of the telomere by measuring the fluorescence of first fluorescently labeled nucleotide at the telomere repeat location, wherein the fluorescently labeled subtelomeric sequence is used as a barcode to identify the chromosome.

5. The method according to any one of claims 1 to 4, wherein the length of the telomere is determined by comparing the intensity of fluorescence to a standard.

6. The method according to any of claim 3 or 4, wherein the second guide RNA comprises multiple guide RNAs, each guide RNA having a portion complementary to a different target sequence in the subtelomeric region of the DNA, wherein each subtelomeric sequence is detected via fluorescent label, thus providing a barcode of a portion of the genomic DNA.

7. The method according to claim 1 or 3, where steps a) and b) are performed after steps c) and d).

8. The method according to claim 2 or 4, where step a) is performed after step b).

9. The method according to any one of claims 1 to 8, wherein the guide RNA comprises a crRNA and a tracrRNA.

10. The method according to any one of claims 1 to 8, wherein the guide RNA is a single gRNA sequence.

11. The method according to any one of claims 1 to 8, where the guide RNA and the Cas9 nickase are contacted with each other to form a complex, prior to contacting with the genomic DNA.

12. The method according to any one of claims 1 to 8, wherein the Cas9 nickase is Cas9 D10A or H840A.

13. The method according to any one of claims 1 to 8, wherein the fluorescently labeled motif sequences are used as a barcode to identify the chromosome.

14. The method according to any one of claims 1 to 8, further comprising ligating the labeled DNA with a ligase.

15. The method according to any one of claims 1 to 8, further comprising linearizing and imaging the labeled genomic DNA in a nanochannel, nanopores or nanogaps or nanochannels.

16. The method according to any one of claims 1 to 8, further comprising linearizing and imaging the labeled genomic DNA on a modified surface.

17. The method according to claim 15 or 16, comprising transporting the genomic DNA into a nanochannel and maintaining the DNA in elongated form in the nanochannel.

18. The method according to any one of claims 1 to 8, further comprising staining the DNA backbone.

19. The method according to any one of claim 1 or 3, wherein the second nicking endonuclease is Nt.BspQI.

20. The method according to any one of claim 1 or 3, wherein the telomere repeat sequence, the motif sequence, or both is present in more than one location in the genomic DNA.

21. The method according to any one of claim 2 or 4, wherein the telomere repeat sequence, the subtelomeric sequence, or both is present in more than one location in the genomic DNA.

22. A method of detecting an individual haplotype, the method comprising:

a) contacting genomic DNA with a guide RNA having a portion complementary to a target genomic sequence directly adjacent to a protospacer adjacent motif (PAM), wherein the target genomic sequence or PAM sequence contain different alleles on the maternal or paternal genomic DNA;

b) contacting gRNA with Cas9 nickase to produce a single-strand nick in the genomic DNA at either maternal or paternal DNA containing the sequence perfectly complementary to the target genomic sequence or PAM sequence, wherein the either maternal or paternal DNA which does not have the perfectly complementary target genomic or PAM sequence is not nicked;
c) contacting the nicked DNA with a polymerase and fluorescently labeled nucleotide, wherein the fluorescently labeled nucleotides are incorporated into the nicked DNA at the target genomic or PAM sequence; and
d) detecting the presence of the perfectly matching alleles by detecting the fluorescence of the first fluorescently labeled nucleotide at the target genomic or PAM sequence.

23. The method according to claim 22, further comprising
e) contacting the genomic DNA with a second nicking endonuclease which is specific for a sequence motif in the genomic DNA thereby producing a second nick in the genomic DNA at the motif sequence;
f) contacting the nicked DNA with a polymerase and second fluorescently labeled nucleotide of different color, wherein the second fluorescently labeled nucleotide is incorporated into the nicked DNA at the motif sequence location, wherein the fluorescently labeled motif sequences are used as a barcode to identify the chromosome.

24. The method according to claim 22, wherein the genomic DNA is contacted with multiple guide RNAs, each guide RNA having a portion perfectly complementary to a different allele in either the maternal or paternal DNA target genomic or PAM sequence, wherein each allele is detected via fluorescent label, thus providing a haplotype of a portion of the genomic DNA.

25. The method according to any one of claims 21 to 24, wherein the guide RNA comprises a crRNA and a tracrRNA.

26. The method according to any one of claims 21 to 24, wherein the guide RNA is a single gRNA sequence.

27. The method according to any one of claims 21 to 24, where the guide RNA and the Cas9 nickase are contacted with each other to form a complex, prior to contacting with the genomic DNA.

28. The method according to any one of claims 21 to 24, wherein the Cas9 nickase is Cas9 D10A or H840A.

29. The method according to any one of claims 21 to 24, wherein the fluorescently labeled motif sequences are used as a barcode to identify the chromosome.

30. The method according to any one of claims 21 to 24, further comprising ligating the labeled DNA with a ligase.

31. The method according to any one of claims 21 to 24, further comprising linearizing and imaging the labeled genomic DNA in a nanochannel, nanopores or nanogaps or nanochannels.

32. The method according to any one of claims 21 to 24, further comprising linearizing and imaging the labeled genomic DNA on a modified surface.

33. The method according to claim 31 or 32, comprising transporting the genomic DNA into a nanochannel and maintaining the DNA in elongated form in the nanochannel.

34. The method according to any one of claims 21 to 24, further comprising staining the DNA backbone.

35. The method according to any one of claims 21 to 24, wherein the second nicking endonuclease is Nt.BspQI.

36. The method according to any one of claims 21 to 35, wherein the identification of multiple alleles is combined to determine a haplotype.

37. A method of labeling genomic DNA:
a) contacting genomic DNA with a guide RNA having a portion complementary a first target sequence in the genomic DNA and with Cas9 nickase to produce a single-strand break in the genomic DNA at the first target sequence;
b) contacting the nicked DNA with a polymerase and fluorescently labeled nucleotide, wherein the fluorescently labeled nucleotide is incorporated into the nicked DNA at the first target sequence;
c) contacting the genomic DNA with a second nicking endonuclease which is specific for a sequence motif in the genomic DNA thereby producing a second nick in the genomic DNA at the motif sequence;
d) contacting the nicked DNA with a polymerase and second fluorescently labeled nucleotide of the same color or different color, wherein the second fluorescently labeled nucleotide is incorporated into the nicked DNA at the motif sequence location.

38. A method of labeling genomic DNA:
a) contacting genomic DNA with a guide RNA having a portion complementary a first target sequence in the genomic DNA and with Cas9 nickase to produce a single-strand break in the genomic DNA at the first target sequence;
b) contacting the nicked DNA with a polymerase and fluorescently labeled nucleotide, wherein the fluorescently labeled nucleotide is incorporated into the nicked DNA at the first target sequence;
c) contacting the genomic DNA with a second guide RNA having a portion complementary to a second target sequence the genomic DNA and with Cas9 nickase to produce a single-strand break in the genomic DNA at the second target sequence,
d) contacting the nicked DNA with a polymerase and second fluorescently labeled nucleotide of the same color or different color, wherein the second fluorescently labeled nucleotide is incorporated into the nicked DNA at the second target sequence location.

39. The method according to claim 37 or claim 38, wherein the labeling is used to create a DNA barcode.

40. A method of mapping genomic DNA comprising:
a) contacting genomic DNA with a guide RNA having a portion complementary a first target sequence in the genomic DNA and with Cas9 nickase to produce a single-strand break in the genomic DNA at the first target sequence;
b) contacting the nicked DNA with a polymerase and fluorescently labeled nucleotide, wherein the fluorescently labeled nucleotide is incorporated into the nicked DNA at the first target sequence;
wherein the target sequence is a motif sequence found in the genomic DNA.

41. The method according to claim 40, wherein the target sequence is about 20 nucleotides in length, and the guide RNA has exact complementaritiy to the last 8, 9, 10, 11, 12, 13, or 14 bases of the 20nt target sequence.

42. The method according to claim 40 or 41, wherein the guide RNA has one or two mismatches in the first 8 nt of the target sequence.

43. The method according to claim 40 or 41, wherein the genomic DNA is mapped to find areas of high density of the target sequence.

44. The method according to claim 40 or 41, further comprising
c) contacting genomic DNA with a guide RNA having a portion complementary a second target sequence in the genomic DNA and with Cas9 nickase to produce a single-strand break in the genomic DNA at the first target sequence;
d) contacting the nicked DNA with a polymerase and second fluorescently labeled nucleotide, wherein the second fluorescently labeled nucleotide is incorporated into the nicked DNA at the second target sequence; wherein the second target sequence is a second motif sequence found in the genomic DNA.

45. The method according to claim 44, further comprising performing the method with 3, 4 or 5 target motif sequences and the corresponding number of differently-labeled fluorescent nucleotides.

SEQUENCE LISTING FREE TEXT

The following information is provided for sequences containing free text under numeric identifier <223>.

| SEQ ID NO: (containing free text) | Free text under <223> |
|---|---|
| 1 | <223> A sequence complementary to the 3'-5' strand of the homo sapiens telomere |
| 2 | <223> Sequence of gRNA for DUF1220. |
| 3 | <223> Sequence of gRNA for HIV plasmid. |
| 4 | <223> Sequence of gRNA for HIV plasmid. |
| 5 | <223> Sequence of gRNA for HIV plasmid. |
| 6 | <223> Sequence of gRNA for Chr1q telomere. |

-continued

| SEQ ID NO: (containing free text) | Free text under <223> |
|---|---|
| 7 | <223> Sequence of gRNA for Chr1q subtelomere. |
| 8 | <223> Sequence of gRNA for Chr1q subtelomere. |
| 9 | <223> Sequence of gRNA for Chr1q subtelomere. |
| 10 | <223> Sequence of gRNA for Chr15q subtelomere. |
| 11 | <223> Sequence of gRNA for Chr15q subtelomere. |
| 12 | <223> Sequence of gRNA for Chr11q subtelomere. |
| 13 | <223> Sequence of gRNA for Chr11q subtelomere. |
| 14 | <223> Sequence of gRNA for Chr12p subtelomere. |
| 15 | <223> Sequence of gRNA for Chr12p subtelomere. |
| 16 | <223> Sequence of gRNA for Alu. |
| 17 | <223> locus 1 of haplotype 1 |
| 18 | <223> gRNA |
| 19 | <223> gRNA |
| 20 | <223> gRNA target in the Alu element |
| 21 | <223> gRNA for Chromosome 8q |
| 22 | <223> gRNA for Chromosome 8q |
| 23 | <223> gRNA for Chromosome 8q |

The invention claimed is:

1. A method of detecting an individual haplotype, the method comprising:
   a) contacting genomic DNA with a guide RNA having a portion complementary to a target genomic sequence directly adjacent to a protospacer adjacent motif (PAM), wherein the target genomic sequence or PAM sequence contain different alleles on the maternal or paternal genomic DNA;
   b) contacting gRNA with Cas9 nickase to produce a single-strand nick in the genomic DNA at either maternal or paternal DNA containing the sequence perfectly complementary to the target genomic sequence or PAM sequence, wherein the either maternal or paternal DNA which does not have the perfectly complementary target genomic or PAM sequence is not nicked;
   c) contacting the nicked DNA with a polymerase and fluorescently labeled nucleotide, wherein the fluorescently labeled nucleotides are incorporated into the nicked DNA at the target genomic or PAM sequence; and
   d) detecting the presence of the sequence perfectly complementary to the target genomic sequence or PAM sequence by detecting the fluorescence of the first fluorescently labeled nucleotide at the target genomic or PAM sequence
   wherein, the haplotype is determined by the detection of said alleles.

2. The method according to claim 1, further comprising
   a) contacting the genomic DNA with a second nicking endonuclease which is specific for a sequence motif in the genomic DNA thereby producing a second nick in the genomic DNA at the motif sequence;
   b) contacting the nicked DNA with a polymerase and second fluorescently labeled nucleotide of different color, wherein the second fluorescently labeled nucleotide is incorporated into the nicked DNA at the motif sequence location, wherein the fluorescently labeled motif sequences are used as a barcode to identify the chromosome.

3. The method according to claim 1, wherein the genomic DNA is contacted with multiple guide RNAs, each guide RNA having a portion perfectly complementary to a different allele in either the maternal or paternal DNA target genomic or PAM sequence, wherein each allele is detected via fluorescent label, thus providing a haplotype of a portion of the genomic DNA.

4. The method according to claim 1, wherein the identification of multiple alleles is combined to determine a haplotype.

5. The method according to claim 1, wherein the fluorescently labeled sequences are used as a barcode to identify the chromosome.

6. The method according to claim 1, further comprising ligating the labeled DNA with a ligase.

7. The method according to claim 1, wherein the target sequence is about 20 nucleotides in length, and the guide RNA has exact complementarity to the last 10, 11, or 12 bases of the 20 nucleotide target sequence.

8. The method according to claim 1, wherein the guide RNA has one or two mismatches in the first 8 nucleotides of the target sequence.

9. The method according to claim 1, wherein the guide RNA comprises a crRNA and a tracrRNA.

10. The method according to claim 1, wherein the guide RNA is a single gRNA sequence.

11. The method according to claim 1, wherein the guide RNA and the Cas9 nickase are contacted with each other to form a complex, prior to contacting with the genomic DNA.

12. The method according to claim 1, wherein the Cas9 nickase is Cas9 D10A or H840A.

* * * * *

SEQUENCE LISTING

```
<160> NUMBER OF SEQ ID NOS: 33

<210> SEQ ID NO 1
<211> LENGTH: 20
<212> TYPE: RNA
<213> ORGANISM: Artificial Sequence
<220> FEATURE:
<223> OTHER INFORMATION: A sequence complementary to the 3'-5' strand of
      the homo sapiens telomere

<400> SEQUENCE: 1
uuaggguuag gguuaggguu                                              20

<210> SEQ ID NO 2
<211> LENGTH: 20
<212> TYPE: RNA
<213> ORGANISM: Artificial Sequence
<220> FEATURE:
<223> OTHER INFORMATION: Sequence of gRNA for DUF1220.

<400> SEQUENCE: 2
aaguuccuuu uaugcauugg                                              20

<210> SEQ ID NO 3
<211> LENGTH: 24
<212> TYPE: DNA
<213> ORGANISM: Artificial Sequence
<220> FEATURE:
<223> OTHER INFORMATION: Sequence of gRNA for HIV plasmid.

<400> SEQUENCE: 3
caccgcagga tatgtaactg acag                                         24

<210> SEQ ID NO 4
<211> LENGTH: 24
<212> TYPE: DNA
<213> ORGANISM: Artificial Sequence
<220> FEATURE:
<223> OTHER INFORMATION: Sequence of gRNA for HIV plasmid.

<400> SEQUENCE: 4
caccggccag atgagagaac caag                                         24
```

```
<210> SEQ ID NO 5
<211> LENGTH: 25
<212> TYPE: DNA
<213> ORGANISM: Artificial Sequence
<220> FEATURE:
<223> OTHER INFORMATION: Sequence of gRNA for HIV plasmid.

<400> SEQUENCE: 5
caccgagagt aagtctctca agcgg                                              25

<210> SEQ ID NO 6
<211> LENGTH: 20
<212> TYPE: RNA
<213> ORGANISM: Artificial Sequence
<220> FEATURE:
<223> OTHER INFORMATION: Sequence of gRNA for Chr1q telomere.

<400> SEQUENCE: 6
uuaggguuag gguuaggguu                                                    20

<210> SEQ ID NO 7
<211> LENGTH: 20
<212> TYPE: RNA
<213> ORGANISM: Artificial Sequence
<220> FEATURE:
<223> OTHER INFORMATION: Sequence of gRNA for Chr1q subtelomere.

<400> SEQUENCE: 7
ccccuguugc cagagccagu                                                    20

<210> SEQ ID NO 8
<211> LENGTH: 20
<212> TYPE: RNA
<213> ORGANISM: Artificial Sequence
<220> FEATURE:
<223> OTHER INFORMATION: Sequence of gRNA for Chr1q subtelomere.

<400> SEQUENCE: 8
guauuuaguc agagggcuag                                                    20

<210> SEQ ID NO 9
<211> LENGTH: 20
<212> TYPE: RNA
<213> ORGANISM: Artificial Sequence
<220> FEATURE:
<223> OTHER INFORMATION: Sequence of gRNA for Chr1q subtelomere.

<400> SEQUENCE: 9
auacaguagg auaaccgcaa                                                    20

<210> SEQ ID NO 10
<211> LENGTH: 20
<212> TYPE: RNA
<213> ORGANISM: Artificial Sequence
<220> FEATURE:
<223> OTHER INFORMATION: Sequence of gRNA for Chr15q subtelomere.

<400> SEQUENCE: 10
accuugcuac cacgagagca                                                    20

<210> SEQ ID NO 11
<211> LENGTH: 20
<212> TYPE: RNA
<213> ORGANISM: Artificial Sequence
<220> FEATURE:
<223> OTHER INFORMATION: Sequence of gRNA for Chr15q subtelomere.
```

```
<400> SEQUENCE: 11
uccauugguu uaauuaggaa                                               20

<210> SEQ ID NO 12
<211> LENGTH: 20
<212> TYPE: RNA
<213> ORGANISM: Artificial Sequence
<220> FEATURE:
<223> OTHER INFORMATION: Sequence of gRNA for Chr11q subtelomere.

<400> SEQUENCE: 12
gguccacccu acagaugugc                                               20

<210> SEQ ID NO 13
<211> LENGTH: 20
<212> TYPE: RNA
<213> ORGANISM: Artificial Sequence
<220> FEATURE:
<223> OTHER INFORMATION: Sequence of gRNA for Chr11q subtelomere.

<400> SEQUENCE: 13
agaucagcag ccacgugugc                                               20

<210> SEQ ID NO 14
<211> LENGTH: 20
<212> TYPE: RNA
<213> ORGANISM: Artificial Sequence
<220> FEATURE:
<223> OTHER INFORMATION: Sequence of gRNA for Chr12p subtelomere.

<400> SEQUENCE: 14
accuugcuac cacgagagca                                               20

<210> SEQ ID NO 15
<211> LENGTH: 20
<212> TYPE: RNA
<213> ORGANISM: Artificial Sequence
<220> FEATURE:
<223> OTHER INFORMATION: Sequence of gRNA for Chr12p subtelomere.

<400> SEQUENCE: 15
uccauugguu uaauuaggaa                                               20

<210> SEQ ID NO 16
<211> LENGTH: 20
<212> TYPE: RNA
<213> ORGANISM: Artificial Sequence
<220> FEATURE:
<223> OTHER INFORMATION: Sequence of gRNA for Alu.

<400> SEQUENCE: 16
uguaauccca gcacuuuggg                                               20

<210> SEQ ID NO 17
<211> LENGTH: 24
<212> TYPE: DNA
<213> ORGANISM: Artificial Sequence
<220> FEATURE:
<223> OTHER INFORMATION: locus 1 of haplotype 1

<400> SEQUENCE: 17
aaccattcaa acggcgattg cgtg                                          24

<210> SEQ ID NO 18
<211> LENGTH: 20
```

```
<212> TYPE: DNA
<213> ORGANISM: Artificial Sequence
<220> FEATURE:
<223> OTHER INFORMATION: gRNA

<400> SEQUENCE: 18
ccaaggccga caaagtccag                                                  20

<210> SEQ ID NO 19
<211> LENGTH: 20
<212> TYPE: DNA
<213> ORGANISM: Artificial Sequence
<220> FEATURE:
<223> OTHER INFORMATION: gRNA

<400> SEQUENCE: 19
aaaaccaaga atccttttgt                                                  20

<210> SEQ ID NO 20
<211> LENGTH: 17
<212> TYPE: DNA
<213> ORGANISM: Artificial Sequence
<220> FEATURE:
<223> OTHER INFORMATION: gRNA target in the Alu element

<400> SEQUENCE: 20
gcctataatc ccagcac                                                     17

<210> SEQ ID NO 21
<211> LENGTH: 23
<212> TYPE: DNA
<213> ORGANISM: Artificial Sequence
<220> FEATURE:
<223> OTHER INFORMATION: gRNA for Chromosome 8q

<400> SEQUENCE: 21
tccagactta tgccactgag agg                                              23

<210> SEQ ID NO 22
<211> LENGTH: 23
<212> TYPE: DNA
<213> ORGANISM: Artificial Sequence
<220> FEATURE:
<223> OTHER INFORMATION: gRNA for Chromosome 8q

<400> SEQUENCE: 22
taaataccac aaggaaatct tgg                                              23

<210> SEQ ID NO 23
<211> LENGTH: 23
<212> TYPE: DNA
<213> ORGANISM: Artificial Sequence
<220> FEATURE:
<223> OTHER INFORMATION: gRNA for Chromosome 8q

<400> SEQUENCE: 23
accctattcc tttaaaagcc agg                                              23

<210> SEQ ID NO 24
<211> LENGTH: 16
<212> TYPE: DNA
<213> ORGANISM: Homo sapiens
<220> FEATURE:
<221> NAME/KEY: misc_feature
<222> LOCATION: (10)..(10)
<223> OTHER INFORMATION: n is a, c, g, or t
```

```
<400> SEQUENCE: 24
atgctcttcn gtgatc                                                    16

<210> SEQ ID NO 25
<211> LENGTH: 16
<212> TYPE: DNA
<213> ORGANISM: Homo sapiens
<220> FEATURE:
<221> NAME/KEY: misc_feature
<222> LOCATION: (7)..(7)
<223> OTHER INFORMATION: n is a, c, g, or t

<400> SEQUENCE: 25
gatcacngaa gagcat                                                    16

<210> SEQ ID NO 26
<211> LENGTH: 38
<212> TYPE: DNA
<213> ORGANISM: Homo sapiens

<400> SEQUENCE: 26
ggttagggtt agggttaggg ttagggttag ggttaggg                             38

<210> SEQ ID NO 27
<211> LENGTH: 38
<212> TYPE: DNA
<213> ORGANISM: Homo sapiens

<400> SEQUENCE: 27
ccctaacccT aaccctaacc ctaaccctaa ccctaacc                             38

<210> SEQ ID NO 28
<211> LENGTH: 52
<212> TYPE: DNA
<213> ORGANISM: Homo sapiens

<400> SEQUENCE: 28
gcacgtactg tttttcttgt tgtggctgaa acggtgactg tgcttgcagt tg             52

<210> SEQ ID NO 29
<211> LENGTH: 53
<212> TYPE: DNA
<213> ORGANISM: Homo sapiens

<400> SEQUENCE: 29
gcacgtcgta ctgtttactt gttgtgaaac cgagagtcct gtgcatgcag ttg            53

<210> SEQ ID NO 30
<211> LENGTH: 51
<212> TYPE: DNA
<213> ORGANISM: Homo sapiens

<400> SEQUENCE: 30
gcacgtactg ctcttctgtt gtggctgaaa cggtgactgg ctcttcagtt g              51

<210> SEQ ID NO 31
<211> LENGTH: 53
<212> TYPE: DNA
<213> ORGANISM: Homo sapiens

<400> SEQUENCE: 31
gcacgtcgta ctgctcttct gttgtgaaac ggagagtcct ggctcttcag ttg            53
```

```
<210> SEQ ID NO 32
<211> LENGTH: 50
<212> TYPE: DNA
<213> ORGANISM: Homo sapiens

<400> SEQUENCE: 32
gcacgactgc tcttctgtgg tggctgaaac ggtgactgct cttctagttg                50

<210> SEQ ID NO 33
<211> LENGTH: 55
<212> TYPE: DNA
<213> ORGANISM: Homo sapiens

<400> SEQUENCE: 33
gcacgtcgta ctgctcttct gtcgtgaaac ggtgactccg ctgctcttct agttg          55
```